United States Patent
Zustiak

(10) Patent No.: US 12,398,255 B2
(45) Date of Patent: Aug. 26, 2025

(54) BIOCOMPATIBLE CROSSLINKERS FOR CONTROLLED DEGRADATION OF POLYMER HYDROGELS

(71) Applicant: Saint Louis University, St. Louis, MO (US)

(72) Inventor: Silviya Petrova Zustiak, St. Louis, MO (US)

(73) Assignee: Saint Louis University, St. Louis, MO (US)

(*) Notice: Subject to any disclaimer, the term of this patent is extended or adjusted under 35 U.S.C. 154(b) by 351 days.

(21) Appl. No.: 17/201,522

(22) Filed: Mar. 15, 2021

(65) Prior Publication Data

US 2021/0292513 A1 Sep. 23, 2021

Related U.S. Application Data

(60) Provisional application No. 62/990,761, filed on Mar. 17, 2020.

(51) Int. Cl.
| | |
|---|---|
| C08K 5/00 | (2006.01) |
| A61L 24/04 | (2006.01) |
| A61L 26/00 | (2006.01) |
| C08L 71/02 | (2006.01) |

(52) U.S. Cl.
CPC .......... *C08K 5/0025* (2013.01); *A61L 24/046* (2013.01); *A61L 26/0019* (2013.01); *A61L 26/008* (2013.01); *C08L 71/02* (2013.01); *C08L 2203/02* (2013.01)

(58) Field of Classification Search
None
See application file for complete search history.

(56) References Cited

U.S. PATENT DOCUMENTS

| 8,410,189 B2 | 4/2013 | Carnahan et al. |
| 9,968,558 B2 * | 5/2018 | Sell ...................... A61K 38/385 |
| 2012/0177592 A1 | 7/2012 | Radosz et al. |

OTHER PUBLICATIONS

Kharkar et al., Thiol-ene click hydrogels for therapeutic delivery. ACS Biomater Sci Eng. Feb. 8, 2016;2(2):165-179. (Year: 2016).*
Macdougall et al., Efficient In Situ Nucleophilic Thiol-yne Click Chemistry for the Synthesis of Strong Hydrogel Materials with Tunable Properties, CS Macro Letters 2017 6 (2), 93-97 (Year: 2017).*
Zustiak, Silviya P., and Jennie B. Leach. "Hydrolytically degradable poly (ethylene glycol) hydrogel scaffolds with tunable degradation and mechanical properties." Biomacromolecules 11.5 (2010): 1348-1357 and Supplemental information (Year: 2010).*
Zustiak et al., Hydrolytically degradable poly(ethylene glycol) hydrogel scaffolds with tunable degradation and mechanical properties; Biomacromolecules; 2010, vol. 11, No. 5, pp. 1348-1357.

* cited by examiner

*Primary Examiner* — Jennifer Chin
(74) *Attorney, Agent, or Firm* — Steven T. Kazmierski; Sandberg Phoenix & von Gontard PC

(57) ABSTRACT

The present disclosure relates generally to hydrogel biomaterials. In particular, the present disclosure is directed to compositions and methods for developing hydrolytically degradable hydrogels.

19 Claims, 22 Drawing Sheets
(22 of 22 Drawing Sheet(s) Filed in Color)

BIOCOMPATIBLE CROSSLINKERS FOR CONTROLLED DEGRADATION OF POLYMER HYDROGELS

CROSS-REFERENCE TO RELATED APPLICATIONS

This application claims priority to U.S. Provisional Patent Application No. 62/990,761, filed on Mar. 17, 2020, which is hereby incorporated by reference in its entirety.

BACKGROUND OF THE DISCLOSURE

The present disclosure relates generally to hydrogel biomaterials. In particular, the present disclosure is directed to compositions and methods for developing hydrolytically degradable hydrogels.

Hydrogel biomaterials have been extensively studied due to their ability to form swellable networks with properties mimicking soft biological tissues. Hydrogels are also useful as delivery systems for protein, drug, and nucleic acids, as substrates for basic biological research, as matrices for cell encapsulation and transplantation, and as in vitro models for drug screening. Biodegradable hydrogels are particularly valuable because they allow native tissue regeneration and modulate drug and cell delivery in matrix-type devices, without the need for removal surgeries.

Degradable hydrogels can be formed from both natural and synthetic polymers. Enzymatic and hydrolytic degradation are the two major physiologically relevant mechanisms that confer degradability to hydrogel matrices. One widely used synthetic hydrogel is poly(ethylene glycol) (PEG), which has the advantages of being non-immunogenic, inert, and biocompatible. PEG polymer is not degradable under physiological conditions, however. Thus, degradable moieties must be introduced to fabricate degradable PEG hydrogels.

Techniques employed to impart degradation to PEG hydrogels include incorporating enzymatically cleavable peptide crosslinkers or hydrolytically degradable monomers or copolymers, such as polylactic acid (PLA) and poly glycolic acid (PGA). All of these methods have advantages and drawbacks. For example, peptide crosslinkers' reliance on enzymes can result in inconsistent degradation rates. PEG-PLA and PEG-PGA hydrogels are hydrolytically degradable, but can be associated with protein denaturation due to the copolymer hydrophobicity and acidic degradation products. In another example, multiarm PEG-amine crosslinked with an ester-containing amine-reactive PEG derivative has been described as a hydrolytically degradable scaffold for protein delivery. This polymer was entirely hydrophilic, but the nonspecific crosslinking reaction may lead to covalent bonding between the polymer network and the encapsulated proteins. Thus drawback has been alleviated using PEG-multiacrylates and PEG-dithiols to form fully hydrophilic hydrogels with highly specific crosslinking chemistry. However, control of degradation of these hydrogels is limited. The dithiol crosslinkers presently available offer little variability in degradation rates, which restricts their application. Other ways to control hydrogel degradation include varying the polymer molecular weight, using different end-functionalities of these PEG macromer, and varying the molar ratio of the reactive groups. However, these methods significantly affect hydrogel mechanical and physical properties.

Accordingly, there exists a need for compositions and methods for controlling hydrogel degradation. The crosslinkers of the present disclosure provide for controlled gelation kinetics and crosslinking density with only minor changes in hydrogel properties. Hydrogels of the present disclosure are useful in a variety of tissue engineering and drug delivery applications due to their controlled gelation and degradation.

BRIEF DESCRIPTION OF THE DISCLOSURE

In one aspect, the present disclosure is directed to a hydrogel crosslinker of formula (I),

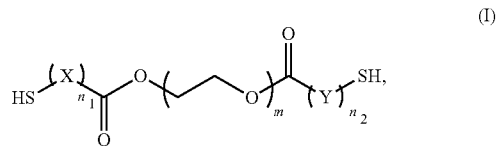

wherein m is at least 10 repeating units; $n_1$ and $n_2$ ranges from 1 to 5 repeating units; X and Y are independently selected from C, $CR^1$, $NR^2$, O, $SR^3$, and aryl; and $R^1$, $R^2$, and $R^3$ are independently selected from H, alkyl, alkoxy, aryl, hydroxyl, amino, nitro, carboxyl, a halogen, a polar pendant group, and a non-polar pendant group.

In one aspect, the present disclosure is directed to a hydrolytically degradable hydrogel comprising a crosslinker of formula (I),

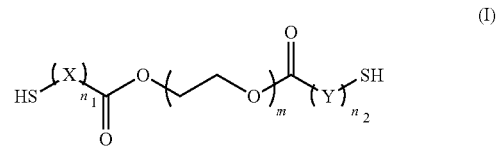

wherein m is at least 10 repeating units; $n_1$ and $n_2$ ranges from 1 to 5 repeating units; X and Y are independently selected from C, $CR^1$, $NR^2$, O, $SR^3$, and aryl; and $R^1$, $R^2$, and $R^3$ are independently selected from H, alkyl, alkoxy, aryl, hydroxyl, amino, nitro, carboxyl, a halogen, a polar pendant group, and a non-polar pendant group; and a polymer.

In one aspect, the present disclosure is directed to a method of preparing a hydrolytically degradable hydrogel, the method comprising: providing a hydrogel precursor solution; providing to the hydrogel precursor solution a crosslinker of formula (I),

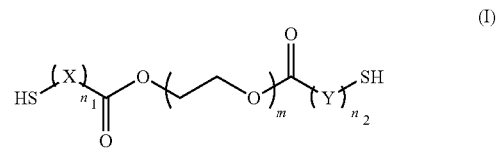

wherein m is at least 10 repeating units; $n_1$ and $n_2$ ranges from 1 to 5 repeating units; X and Y are independently selected from C, $CR^1$, $NR^2$, O, $SR^3$, and aryl; and $R^1$, $R^2$, and $R^3$ are independently selected from H, alkyl, alkoxy, aryl, hydroxyl, amino, nitro, carboxyl, a halogen, a polar pendant group, and a non-polar pendant group; allowing the hydrogel precursor solution and crosslinker to polymerize to form a hydrolytically degradable hydrogel.

BRIEF DESCRIPTION OF THE DRAWINGS

The patent or patent application file contains at least one drawing executed in color. Copies of this patent or patent application publication with color drawings will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein.

DETAILED DESCRIPTION

Unless defined otherwise, all technical and scientific terms used herein have the same meaning as commonly understood by one of ordinary skill in the art to which the disclosure belongs.

In one aspect, the present disclosure is directed to a hydrogel crosslinker of formula (I),

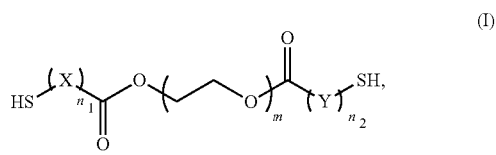

wherein m is at least 10 repeating units; $n_1$ and $n_2$ ranges from 1 to 5 repeating units; X and Y are independently selected from C, $CR^1$, $NR^2$, O, $SR^3$, and aryl; and $R^1$, $R^2$, and $R^3$ are independently selected from H, alkyl, alkoxy, aryl, hydroxyl, amino, nitro, carboxyl, a halogen, a polar pendant group, and a non-polar pendant group. Suitable aryls are phenyl and naphthyl. Suitable alkoxy are methoxy, ethoxy, propoxy, butoxy, pentoxy, hexoxy, heptoxy, octoxy, nonoxy, decoxy, undecoxy, and dodoxy. Suitable halogens include fluro, chloro, bromo, and iodo. Suitable alkyls include methyl, ethyl, propyl, butyl, pentyl, hexyl, heptyl, octyl, nonyl, decyl, undecyl, and dodecyl.

Figure 1:
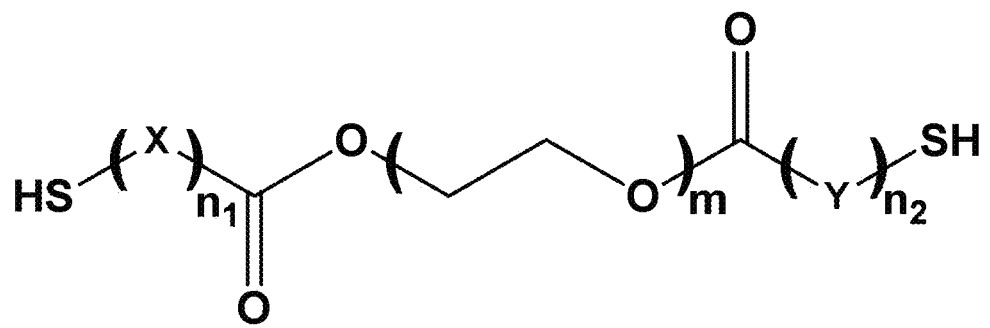
FIG. 1 shows the basic crosslinker structure, where m and n can be a different number of repeating units, and wherein m is greater than 10, and $n_1$ and $n_2$ can range from 1 to 5 repeating units.
Figure 2:
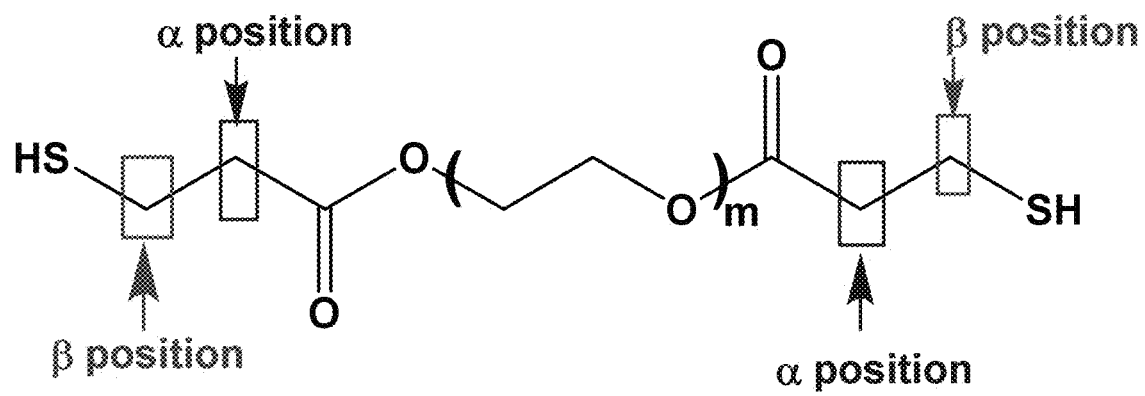
FIG. 2 shows one embodiment of the basic crosslinker structure wherein $n_1=2$ repeating units and $n_2=2$ repeating units, and illustrating a and β positions away from the carbonyl carbon of the ester group, which are modified to impart hydrolytic degradation of the crosslinker.

The positions away from the carbonyl carbon of the ester group are referred to herein as the α position, the β position, the γ position, the δ position, and the ε position. The α position refers to the carbon closest to the carbonyl carbon. As an example, when $n_1$ and $n_2$ are independently 1, the crosslinker would only possess an α position between the carbonyl carbon and thiol. As used herein, the β position refers to the carbon second closest to the carbonyl carbon. As an example, when $n_1$ and $n_2$ are independently 2, the crosslinker would possess an α position and a β position. As used herein, the γ position refers to the carbon third closest to the carbonyl carbon. As an example, when $n_1$ and $n_2$ are independently 3, the crosslinker would possess an α position, a β position, and a γ position. As used herein, the δ position refers to the carbon fourth closest to the carbonyl carbon. As an example, when $n_1$ and $n_2$ are independently 4, the crosslinker would possess an α position, a β position, a γ position and a δ position. As used herein, the F position refers to the carbon fifth closest to the carbonyl carbon. As an example, when $n_1$ and $n_2$ are independently 5, the crosslinker would possess an α position, a β position, a γ position, a δ position, and a ε position. FIG. 2 shows an embodiment of a crosslinker where $n_1$=2 repeating units and $n_2$=2 repeating units, and indicating the α position and the β position.

In one aspect, the present disclosure is directed to a hydrolytically degradable hydrogel comprising a crosslinker of formula (I),

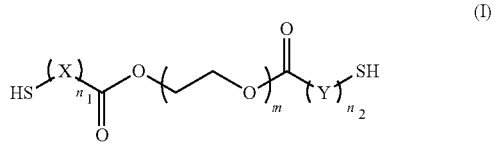

(I)

wherein m is at least 10 repeating units; $n_1$ and $n_2$ ranges from 1 to 5 repeating units; X and Y are independently selected from C, $CR^1$, $NR^2$, O, $SR^3$, and aryl; and $R^1$, $R^2$, and $R^3$ are independently selected from H, alkyl, alkoxy, aryl, hydroxyl, amino, nitro, carboxyl, a halogen, a polar pendant group, and a non-polar pendant group; and a polymer. Suitable aryls are phenyl and naphthyl. Suitable alkoxy are methoxy, ethoxy, propoxy, butoxy, pentoxy, hexoxy, heptoxy, octoxy, nonoxy, decoxy, undecoxy, and dodoxy. Suitable halogens include fluro, chloro, bromo, and iodo. Suitable alkyls include methyl, ethyl, propyl, butyl, pentyl, hexyl, heptyl, octyl, nonyl, decyl, undecyl, and dodecyl.

Suitable polymers can be poly(ethylene glycol) (PEG), poly(enthylene glycol)-di-acrylate (PEG-DA), multi-arm poly(ethylene glycol)-acrylate (PEG-Ac), poly(ethylene glycol)-dithiol (PEG-diSH), poly(ethylene glycol) divinyl sulfone (PEG-diVS), multi-arm poly(ethylene glycol) vinyl sulfone (PEG-VS), poly(enthylene glycol)-di-methacrylate (PEG-DMA), multi-arm poly(ethylene glycol)-methacrylate (PEG-MAc), poly(ethylene glycol)-di-allyl ether (PEG-diAE), multi-arm poly(ethylene glycol)-allyl ether (PEG-AE), poly(ethylene glycol)-di-vinyl ether (PEG-diVE), multi-arm poly(ethylene glycol)-vinyl ether (PEG-VE), poly(ethylene glycol)-di-maleimide (PEG-diMI), multi-arm poly(ethylene glycol)-maleimide (PEG-MI), poly(ethylene glycol)-di-norborene, multi-arm poly(ethylene glycol)-norborene, poly(ethylene glycol)-di-vinyl carbonate, multi-arm poly(ethylene glycol)-vinyl carbonate, polyethylene glycol oligofumarate.

The hydrogel can have a degradation time ranging from minutes to months, including about 18 hours to about 16 days.

The hydrogel can have a gelation time ranging from about 1 minute to about 22 minutes.

The hydrogel can have a storage modulus ranging from about 3 kPa to about 10 kPa.

The hydrogel can have a mesh size ranging from about 7 nm to 13 nm.

The hydrogel can further include a cell.

The hydrogel can further include proteins and drugs.

In one aspect, the present disclosure is directed to a method of preparing a hydrolytically degradable hydrogel, the method comprising: providing a hydrogel precursor solution; providing a crosslinker of formula (I),

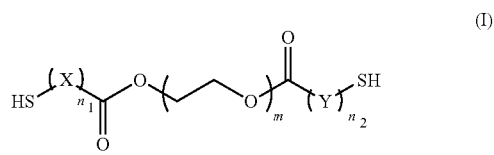

(I)

wherein m is greater than 10 repeating units, $n_1$ and $n_2$ can range from 1 to 5 repeating units, X and Y are independently selected from C, $CR^1$, $NR^2$, O, $SR^3$, and aryl, and $R^1$, $R^2$, and $R^3$ are independently selected from H, alkyl, alkoxy, aryl, hydroxyl, amino, nitro, carboxyl, a halogen, a polar pendant group, and a non-polar pendant group; allowing the hydrogel precursor solution and crosslinker to polymerize to form a hydrolytically degradable hydrogel. Suitable aryls are phenyl and naphthyl. Suitable alkoxy are methoxy, ethoxy, propoxy, butoxy, pentoxy, hexoxy, heptoxy, octoxy, nonoxy, decoxy, undecoxy, and dodoxy. Suitable halogens include fluro, chloro, bromo, and iodo. Suitable alkyls include methyl, ethyl, propyl, butyl, pentyl, hexyl, heptyl, octyl, nonyl, decyl, undecyl, and dodecyl.

The hydrogel precursor solution includes at least one polymer. Suitable polymers include poly(ethylene glycol) (PEG), poly(enthylene glycol)-di-acrylate (PEG-DA), multi-arm poly(ethylene glycol)-acrylate (PEG-Ac), poly(ethylene glycol)-dithiol (PEG-diSH), poly(ethylene glycol) divinyl sulfone (PEG-diVS), multi-arm poly(ethylene glycol) vinyl sulfone (PEG-VS), poly(enthylene glycol)-di-methacrylate (PEG-DMA), multi-arm poly(ethylene glycol)-methacrylate (PEG-MAc), poly(ethylene glycol)-di-allyl ether (PEG-diAE), multi-arm poly(ethylene glycol)-allyl ether (PEG-AE), poly(ethylene glycol)-di-vinyl ether (PEG-diVE), multi-arm poly(ethylene glycol)-vinyl ether (PEG-VE), poly(ethylene glycol)-di-maleimide (PEG-diMI), multi-arm poly(ethylene glycol)-maleimide (PEG-MI), poly(ethylene glycol)-di-norborene, multi-arm poly(ethylene glycol)-norborene, poly(ethylene glycol)-di-vinyl carbonate, multi-arm poly(ethylene glycol)-vinyl carbonate, polyethylene glycol oligofumarate.

The hydrogel can have a degradation time ranging from minutes to months, including about 18 hours to about 16 days.

The hydrogel can have a gelation time ranging from about 1 minute to about 22 minutes.

The hydrogel can have a storage modulus ranging from about 3 kPa to about 10 kPa.

The hydrogel can have a mesh size ranging from about 7 nm to 13 nm.

The method can further include adding a cell to one of the hydrogel precursor solution, the crosslinker, and the hydrolytically degradable hydrogel.

The method can further include adding a protein, a drug, and combinations to one of the hydrogel precursor solution, the crosslinker, and the hydrolytically degradable hydrogel.

EXAMPLE

Example 1

Materials and Methods

Poly(ethylene glycol)-di-acrylate (PEG-DA; 5 kDa), 4-arm PEG-acrylate (4-arm PEG-Ac; 10 kDa), and PEG-dithiol (PEG-diSH; 3.4 kDa) are from Laysan Bio, Inc. (Arab, AL). PEG-OH (3.4 kDa) is from Electron Microscopy Sciences (Hatfield, PA). Dithioerithritol (DTT), penicillin/streptomycin (pen/strep), and 4-mercaptophenylacetic acid is from Millipore Sigma (St. Louis, MO). Thioglycolic acid is from Acros Organics (Geel, Belgium). P-toluenesulfonic acid and fetal bovine serum (FBS) are from VWR (Radnor, PA). 3-mercaptoisobutyric acid and 4-mercaptohydrocinnamic acid are from TCI America (Portland, OR). Toluene, 3-mercaptopropionic acid, 2-mercaptopropionic acid, 5,5 dithio-bis(2-nitrobenzoic acid) (Ellman's reagent), Roswell Park Memorial Institute (RPMI) 1640 Medium, and CellTiter 96® AQueous One Solution Cell Proliferation (MTS) Assay are from ThermoFisher Scientific (Rockford, IL). LIVE/DEAD cell assay is from Invitrogen (Eugene, OR). 3,3'-Dioctadecyloxacarbocyanine Perchlorate (DiOC$_{18}$) is from AAT Bioquest (Sunnyvale, CA). Silicone isolator sheets (0.5 mm thick), from Grace Bio Labs (Bend, OR), were used as spacers. Rain-X® is from a local hardware store. U87 cells are from ATCC (Manassas, VA).

Crosslinker Synthesis

A Fischer esterification reaction was used to synthesize six PEG-diester-dithiol crosslinkers (names in brackets chosen for ease of discussion): PEG-dithiolglycolate (named PEG-diester-dithiol-1 or PEG-DD1), PEG-dithiolpropionate (named PEG-diester-dithiol-2 or PEG-DD2), PEG-di-3-mercaptoisobutyrate (named PEG-diester-dithiol-2-methyl or PEG-DD2M), PEG-di-2-mercaptopropanoate (named PEG-diester-dithiol-1-methyl or PEG-DD1M), PEG-di-4-mercaptophenylacetate (named PEG-diester-dithiol-1-phenyl or PEG-DD1P), and PEG-di-4-mercaptohydrocinnamate (named PEG-diester-dithiol-2-phenyl or PEG-DD2P) (Table 1). First, PEG-OH was dried using azeotropic distillation in toluene under an inert atmosphere of argon. The dried PEG-OH was re-dissolved in anhydrous toluene, and the desired mercaptocarboxylic acid (e.g., mercaptoacetic acid for PEG-DD1) was added at 20-times molar excess to the reaction flask in the presence of DTT (reducing agent; 1 mmol) and p-toluenesulfonic acid (catalyst; 0.4 mmol) and allowed to reflux for 24 hours at ~120° C.-140° C. (temperature of oil bath) under argon with stirring. The product solution was cooled and concentrated under rotary evaporation. The product was precipitated 3 times with ice-cold acetone and recovered via vacuum filtration. The product crosslinkers were dried overnight under vacuum and stored in a desiccating container at −20° C. until use. The average product yield was ~80% and the average derivatization was >90% as confirmed by proton nuclear magnetic resonance ($^1$H NMR).

Table 1. Structures, abbreviations, and pK$_a$ values of crosslinkers synthesized in this study. PEG-diSH was commercially obtained and used as a non-ester-containing reference crosslinker. All crosslinkers had a molecular weight of 3.4 kDa and were water soluble.

| Crosslinker Name | Abbreviation | Chemical Structure | Thiol pK$_a$ |
|---|---|---|---|
| PEG-dithiol | PEG-diSH | HS~~~[O~~~]$_{77}$O~~~SI- | ~10.5-10.7 [44] |
| PEG-diester-dithiol-2 | PEG-DD2 | HS~~~C(O)~[O~~~]$_{77}$O~C(O)~~~SH | ~9.4-9.6 [44] |
| PEG-diester-dithiol-2-methyl | PEG-DD2M | HS~CH(CH$_3$)~C(O)~[O~~~]$_{77}$O~C(O)~CH(CH$_3$)~SH | ~9.4-9.6 [44] |
| PEG-diester-dithiol-1 | PEG-DD1 | HS~C(O)~[O~~~]$_{77}$O~C(O)~SH | ~7.9-8.1 [44, 47] |
| PEG-diester-dithiol-1-methyl | PEG-DD1M | HS~CH(CH$_3$)~[O~~~]$_{77}$O~CH(CH$_3$)~SH (with ester groups) | ~7.9-8.1 [44, 47] |

| Crosslinker Name | Abbreviation | Chemical Structure | Thiol $pK_a$ |
|---|---|---|---|
| PEG-diester-dithiol-1-phenyl | PEG-DD1P | (structure shown) | ~6.5 [52, 53] |
| PEG-diester-dithiol-2-phenyl | PEG-DD2P | (structure shown) | ~6.5 [52, 53] |

Hydrogel Fabrication

All hydrogels used in the Examples were 10% w/v in PEG. First, 20% w/v stock solutions of the 4-arm PEG-Ac and crosslinkers were prepared in 0.3 M triethanolamine (TEA), pH 7.4 immediately before use. Hydrogels were then formed using 4-arm PEG-Ac and PEG-dithiol crosslinkers at a molar ratio of acrylate to thiol of 1:1. The hydrogel precursor solution was mixed well and solution droplets were sandwiched between glass slides coated with RAIN-X and separated by 500 µm spacers. Hydrogels were allowed to gel for 1 hour at 37° C.

Gelation Time

Hydrogel gelation was determined using the inverted tube method. Briefly, hydrogels were prepared as described above in a microfuge tube at room temperature and inverted until the solution stopped flowing upon inversion due to the force of gravity.

Thiol and Acrylate Consumption for Determining Gelation Kinetics and Reaction Efficiency Gelation kinetics and reaction efficiency were measured by thiol consumption as a function of time, using Ellman's assay according to the manufacturer's protocol. All standards and Ellman's reagent (10 mM) were reconstituted in 0.1 M sodium phosphate reaction buffer pH 8 with 1 mM ethylenediaminetetraacetic acid (EDTA). The dithiol crosslinkers were allowed to react with a 3-fold molar excess of PEG-DA (SH:Ac ratio of 1:3). The kinetics of thiol consumption was followed by taking aliquots at predetermined time intervals and diluting 10 times with deionized (DI) water to quench the reaction. Upon completion of the reaction, thiol in each aliquot was estimated by adding 250 µl of reaction buffer and 5 µl of Ellman's reagent (10 mM) to 25 µl of each sample and standard. The mixture was incubated for 15 minutes at room temperature and absorbance was measured at 412 nm using a spectrophotometer (SpectraMax i3, Molecular Devices, Sunnyvale, CA). The reciprocal of thiol molar concentration (1/[SH]) was plotted against time to determine the second-order rate constant as given by the slope of the straight line. Percent thiol consumption was determined by comparing the amount of remaining thiol at the end of the reaction to the initial thiol concentration.

Acrylate consumption was determined using $^1$H NMR (Bruker Avance III HD 700 MHz). Crosslinkers were allowed to react with PEG-DA as described above (a molar excess of at SH:Ac of 1:3) to form a viscous solution and then lyophilized overnight. The samples were dissolved in deuterated water ($D_2O$) at 15 mM. All 1D $^1$H NMR spectra were measured with noesypr1d pulse sequence at 298 K. To estimate acrylate consumption, the ratio of one of the acrylate triplet peaks (5.83 ppm) to the PEG repeat unit (3.52-3.62 ppm) was compared to the same ratio of an unreacted PEG-DA control. The appearance of additional peaks around 2.54-2.83 ppm, where the thioether-ester link formed, indicated qualitatively that the crosslinkers had reacted with the PEG-DA.

Swelling Ratio, Degradation Time, Mesh Size and Crosslink Density

To measure initial swelling ratio, 10% w/v gels (25 µL precursor solution volume) were prepared as previously described and weighed to determine initial mass before swelling ($M_G$). They were then soaked in 1×PBS, pH 7.4 for 4 hours at room temperature. To determine the swollen mass ($M_S$), gels were blotted with a KIMWIPE® and weighed. Gels were dried in an oven at 60° C. for 24 hours and weighed to obtain the dry mass ($M_D$). Initial swelling ratio was calculated as $Q_M = M_S/M_D$.

Additionally, degradation was followed by measuring $Q_M$ as a function of time. $M_S$ was measured at specific time points until gels lacked physical integrity. $Q_M$ was calculated for each time point and normalized to the $Q_M$ of the non-swollen network at time zero ($M_G/M_D$). Initial mesh size ($\xi$) and crosslink density ($v_c$) were calculated via the Flory-Rehner theory.

Rheological Measurements

Rheological measurements were performed using an AR-2000 ex rheometer (TA Instruments) with 20 mm parallel plate geometry. The absence of slip was verified by running experiments with various gap heights. A frequency of 1-10 rad/s and a constant strain of 1%, which was within the linear viscoelastic region, were used for testing all gels. For testing, gels (250 µL, 10% w/v, 500 µm thickness) were equilibrium-swollen for 2 hours at room temperature in PBS, pH 7.4 and cut into discs of 200 mm in diameter. Prior to measurements, excess water from the gel surface was blotted carefully using a KIMWIPE®.

Cell Culture and Maintenance

U87 glioblastoma cells were cultured in RPMI medium, supplemented with 10% FBS and 1% pen/strep in a humidified environment at 37° C. and 5% $CO_2$. For cell maintenance, medium was replaced every 2-3 days until ~80% cell confluency was reached. To subculture, confluent cells were harvested by a 5-minute exposure to 0.05% trypsin/0.02% EDTA.

Cytotoxicity Testing
Cell Viability Upon Encapsulation in 3D Hydrogels

LIVE/DEAD assay was used to assess cell viability according to the manufacturer's protocol. U87 glioblastoma cells were incubated with the fluorescent green membrane stain $DiOC_{18}$ for 24 hours and harvested with trypsin. 4-arm PEG-Ac and the PEG-dithiol crosslinkers were dissolved in 0.3 M TEA and added to the cell suspension to bring the PEG concentration to 10% w/v and the cell concentration to $1 \times 10^6$ cells/mL. The cell-laden gel precursor solution was mixed, pipetted at 30 µL per well of a 24-well plate and incubated for 30 minutes to allow gelation. RPMI medium supplemented with 10% FBS and 1% pen/strep was added to each well to fully cover the gels. Cells seeded on tissue culture polystyrene (TCP) were used as control. All cells were grown for an additional 24 or 48 hours, when fluorescent red nucleolus stain propidium iodide (PI) was added to each well at 0.01 mg/mL to stain necrotic cells. After 1 hour of incubation, images of the cultured cells were taken under a fluorescent microscope (Axiovert 200M; Thornwood, NY) and Image-J software was used to analyze the images. The cell counter plug-in was used to count viable and necrotic cells, and percent cell viability was calculated as the number of live cells divided by the total number of cells×100%.

Hydrogel Leachables and Degradation Products

To evaluate the cytotoxicity of hydrogel leachables and degradation products, 10% w/v gels (50 µL precursor solution volume) were soaked in 500 µL RPMI medium (with 10% v/v FBS and 1% pen/strep) until complete degradation. Medium was collected at 24 and 48 hours and at complete degradation (different gels were used for each time point) and frozen at −20° C. until use. For PEG-DD1, which degraded in less than 24 hours, the 24 hours represented complete gel degradation. U87 cells were seeded at $5 \times 10^4$ cells/mL in a 96-well plate and incubated overnight. Medium was then replaced by conditioned medium (containing leachables or degradation products) and cells were incubated for additional 48 hours. Cell viability was determined with a cell proliferation assay (MTS) according to manufacturer protocol. Absorbance was measured at 490 nm on a spectrophotometer (SpectraMax i3, Molecular Devices, Sunnyvale, CA). Cells cultured in non-conditioned medium were used as controls. Relative percent viability was determined by normalizing the sample absorbance to that of the control.

Statistical Analysis

Results were expressed as average±SD of triplicate samples from three independent experiments. Multiple samples were compared using single factor analysis of variance (ANOVA) followed by a post-hoc analysis. A two-tailed Student's t-test was used to compare between two samples. Differences between data sets were considered significant when $p<0.05$.

Results
Crosslinker Design

A Fischer esterification reaction was used to synthesize six PEG-based diester-dithiol crosslinkers. The non-ester-containing PEG-diSH crosslinker was commercially obtained and used as a control. The crosslinkers were designed to allow a systematic exploration of the effect of their chemical structure on gel degradation kinetics (Table 1). Because the changes in chemical structure resulted in changes in thiol $pK_a$, how the $pK_a$ would affect gel formation was also determined. The $pK_a$ values were obtained from the literature or estimated by comparing crosslinker structures to molecules with similar structures and known $pK_a$. The crosslinker abbreviations were chosen as follows. All crosslinkers were designated as PEG-DD, which stands for PEG-diester-dithiol. To designate the number of methylene groups between the ester and the thiol, the notation 1 and 2 as in PEG-DD1 and PEG-DD2 was used. A pendant methyl group in β position to the carbonyl carbon is designated with an M as in PEG-DD1M. In the aryl crosslinkers, a phenyl group in β position to the thiol is designated with a P as in PEG-DD1P. The chemical structure of PEG-DD2M was chosen, because the methyl group in the vicinity of the ester was expected to impart steric hindrance and increase hydrophobicity, compared to PEG-DD2, prolonging degradation. Similar considerations were applied to PEG-DD1M compared to PEG-DD1. The chemical structures of PEG-DD1P and PEG-DD2P included thiophenyls to study the effects of $pK_a$ and aryl versus alkyl thiols. The phenyl group was also expected to have an electron-withdrawing effect on the carbonyl carbon of the ester group, facilitating degradation.

Gelation Time

Figure 3:
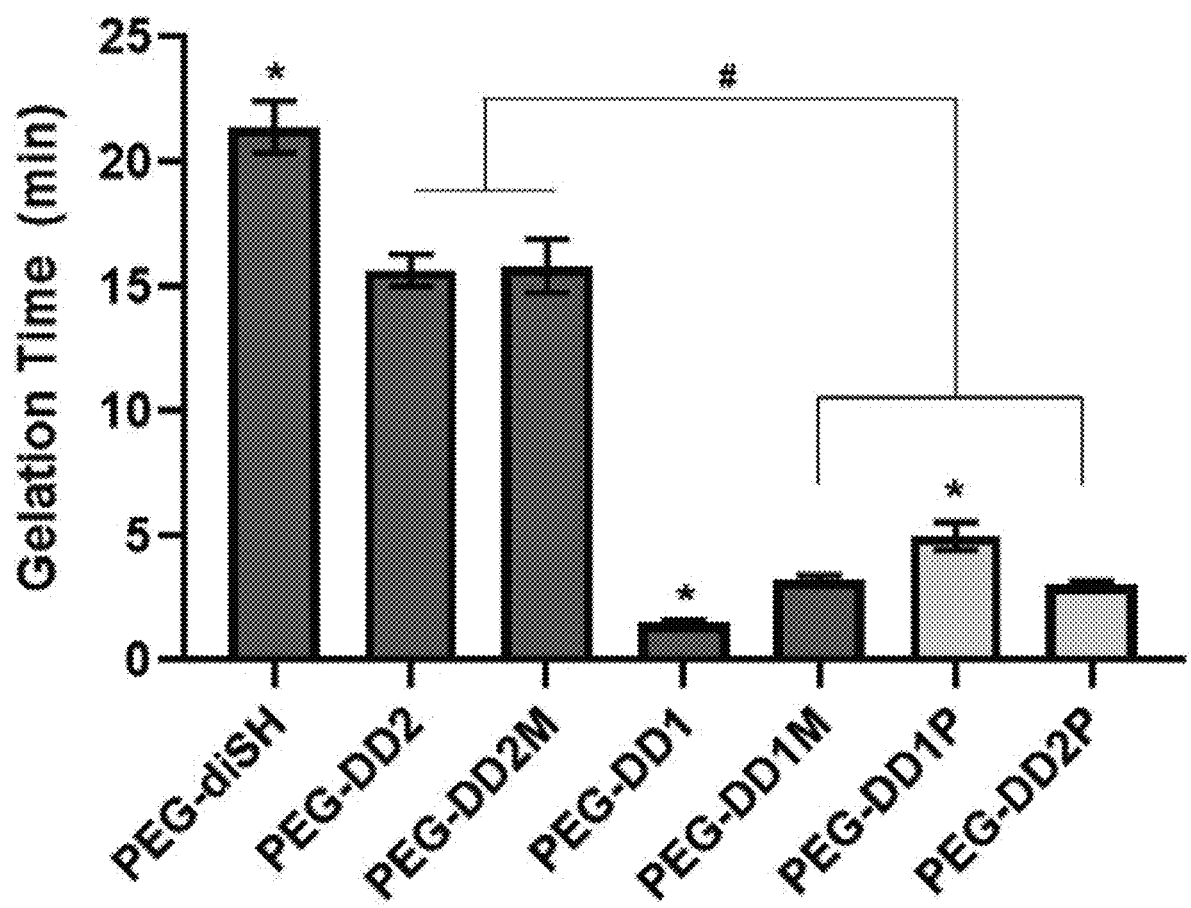
FIG. 3 depicts gelation time for hydrogels formed with 4-arm PEG-Ac and PEG-dithiol crosslinkers. Lightly shaded bars represent aryl crosslinkers. * indicates significance ($p<0.05$) between all groups and # indicates significance ($p<0.05$) between compared groups.
Figure 4A:
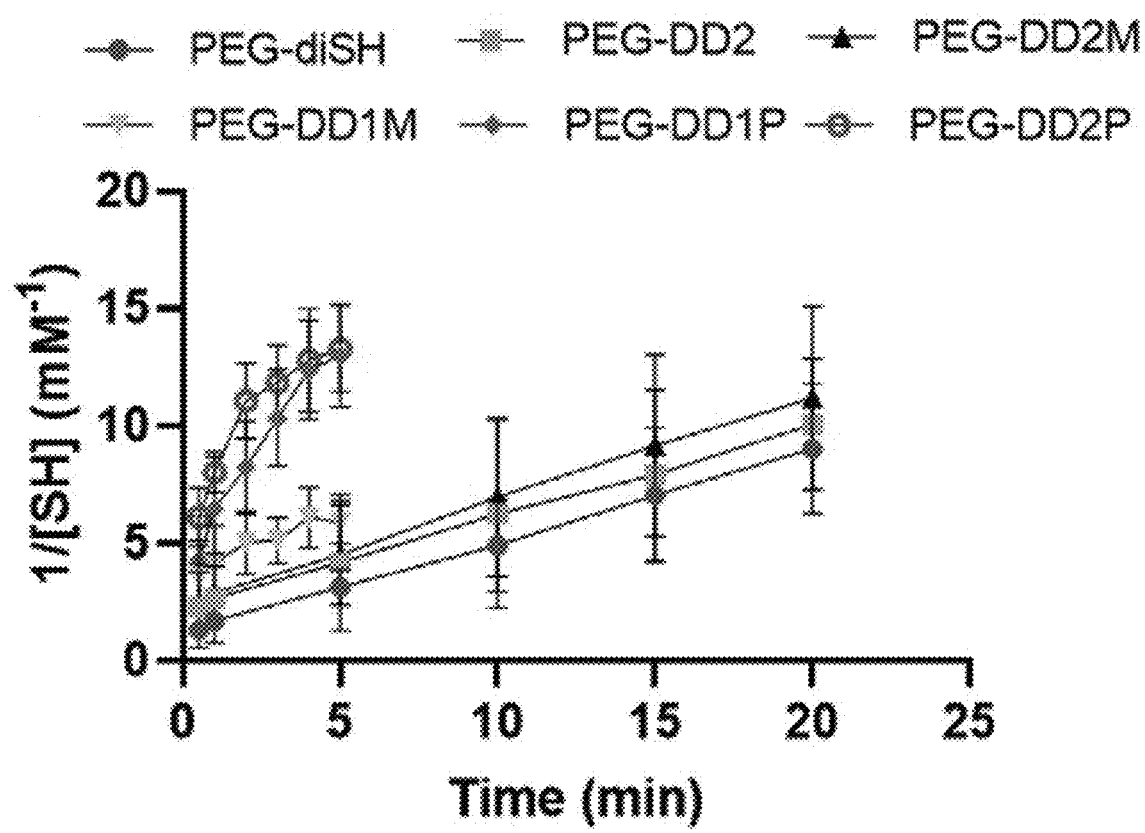
FIGS. 4A-4D depict thiol consumption of hydrogels formed with PEG-diacrylate (PEG-DA) and seven dithiol crosslinkers to show the effect of hydrogel structure on reaction efficiency, as determined by Ellman's assay. Lightly shaded bars represent aryl crosslinkers. Reciprocal of thiol concentration as a function of time for hydrogels crosslinked with dithiol crosslinkers of gelation time >2 minutes (FIG. 4A). Reciprocal of thiol concentration as a function of time for hydrogels formed with PEG-DD1 (FIG. 4B). Percent thiol consumption for hydrogels made with seven dithiol crosslinkers (FIG. 4C). Gelation constant of hydrogels formed with PEG-diacrylate and seven dithiol crosslinkers. # indicates $p<0.05$ for thiol consumption compared to all groups (FIG. 4D).
Figure 4B:
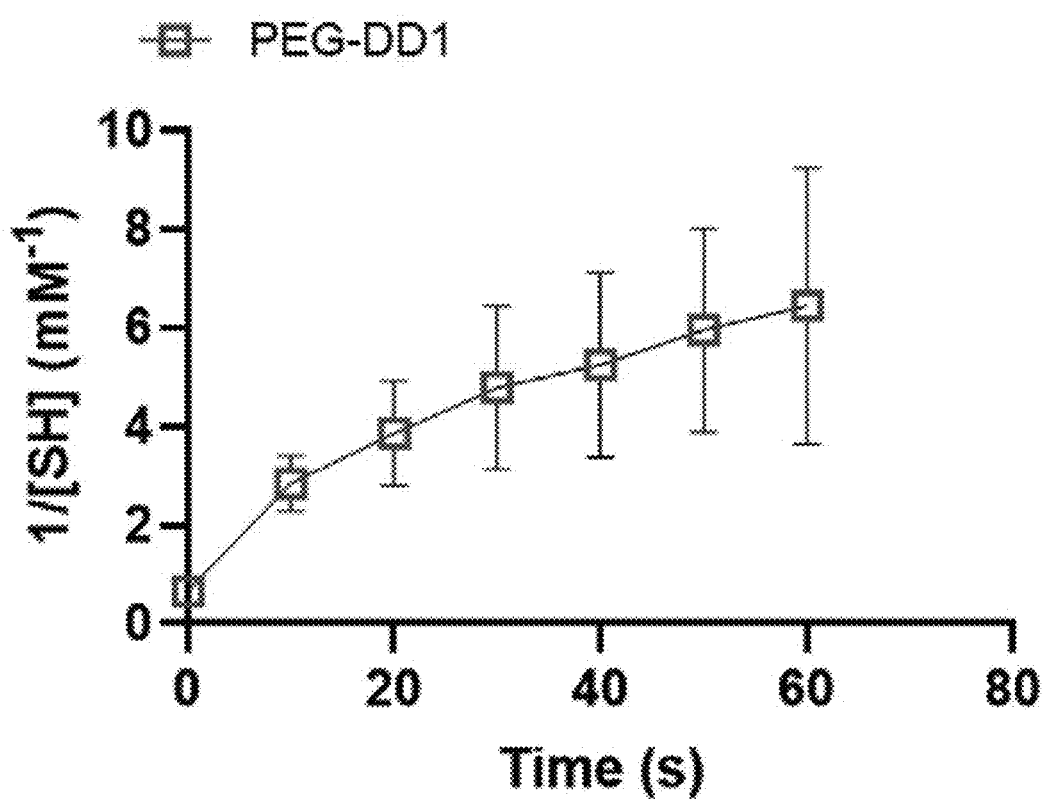
Figure 4C:
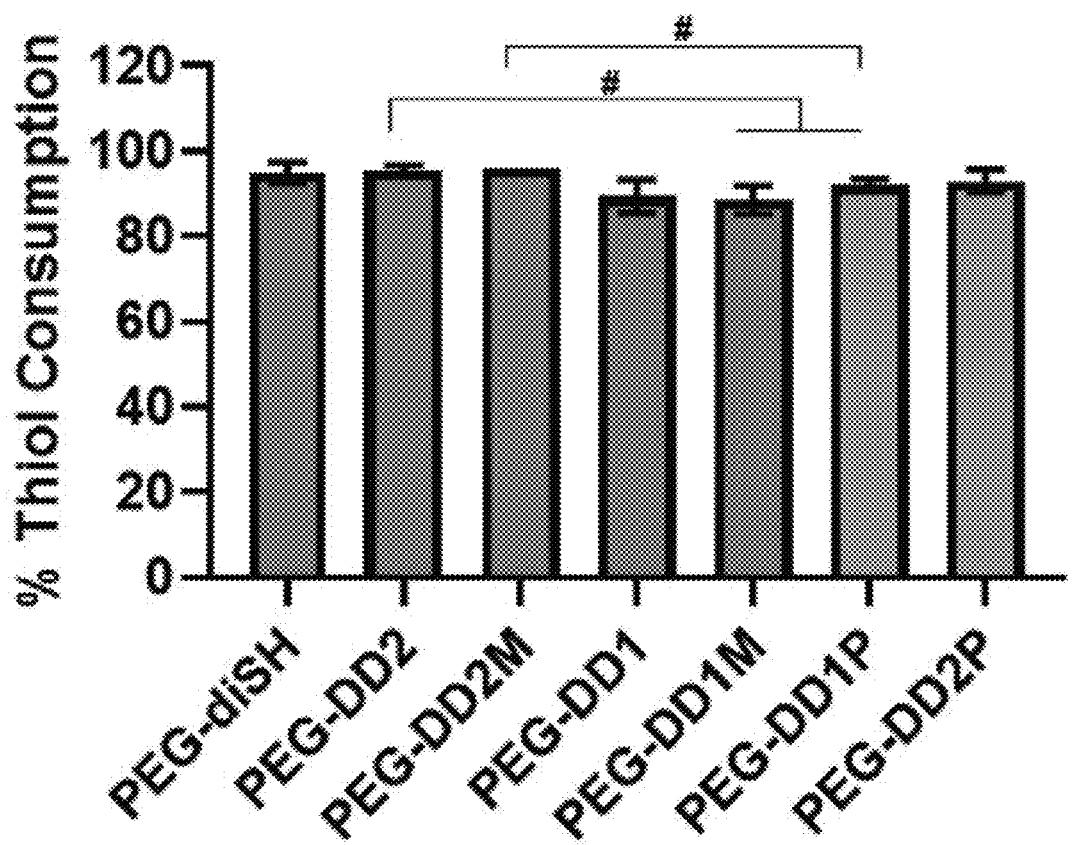
Figure 4D:
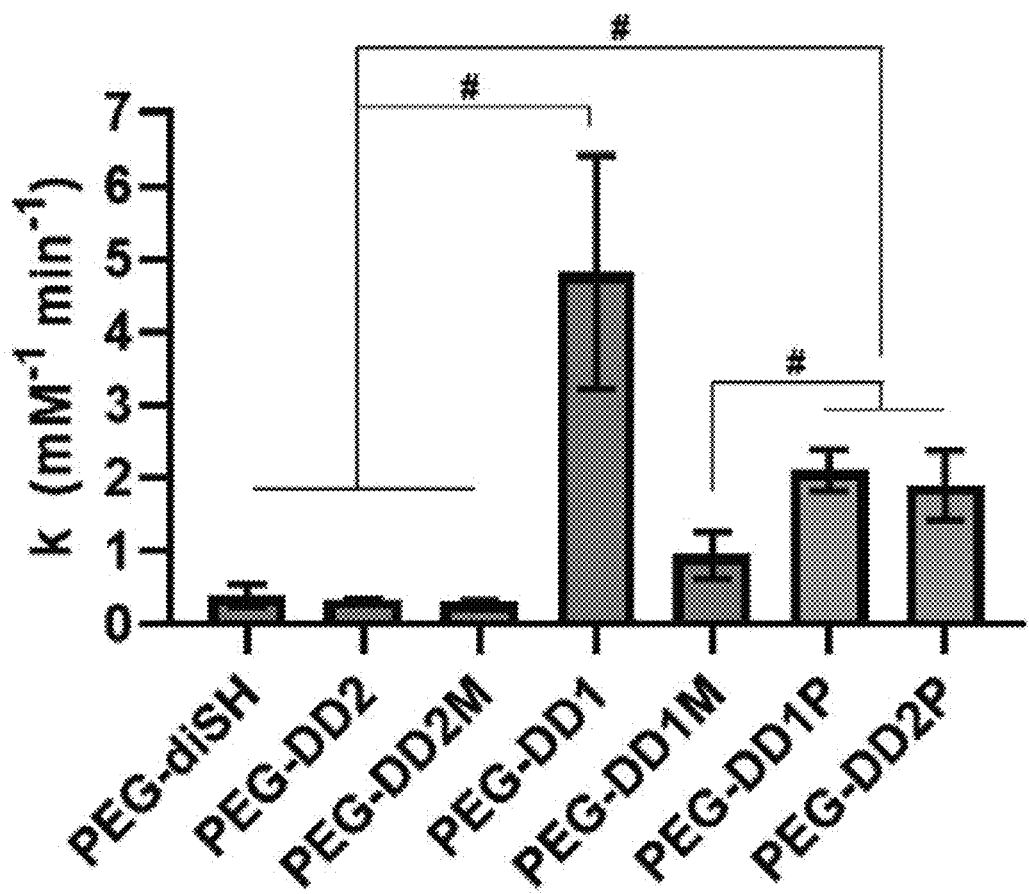

The effect of crosslinker structure on gelation time at a reaction pH of 7.4 was examined (FIG. 3). Note that adjusting the pH to achieve similar gelation time is discussed later. The resulting crosslinker structures presented gelation times ranging from ~90 seconds to 16 minutes, and several trends were observed. Overall, gels prepared with the developed crosslinkers fell into two general categories, fast-gelling (≤5 minutes) and slow-gelling (≥14 minutes). At a constant pH of 7.4, gelation correlated with the thiol $pK_a$. Crosslinkers with a thiol $pK_a<9$ had fast gelation times, while those with a thiol $pK_a>9$ had slow gelation times. Moreover, the chemical structure near the thiol, namely aryl versus alkyl, affected gelation time. Largely, aryl crosslinkers (PEG-DD1P, PEG-DD2P) produced shorter gelation times than alkyl crosslinkers. Incorporating an ester bond in the crosslinker chemical structure significantly decreased gelation times compared to the non-ester-containing control, PEG-diSH. Additionally, gelation time increased with increased hydrophobicity as a result of a pendant methyl group (as in PEG-DD2 vs. PEG-DD2M, PEG-DD1 vs. PEG-DD1M) or longer carbohydrate chain between the ester and the thiol (as in PEG-DD1 vs. PEG-DD2, and PEG-DD1M vs. PEG-DD2M). Further, incorporating electron-withdrawing groups significantly accelerated gelation times (as in PEG-DD2P compared to PEG-DD2 and PEG-DD2M). PEG-DD1 was the fastest-gelling crosslinker, 19-times faster than the slowest, PEG-DD2.

Reaction Efficiency

Figure 5A:
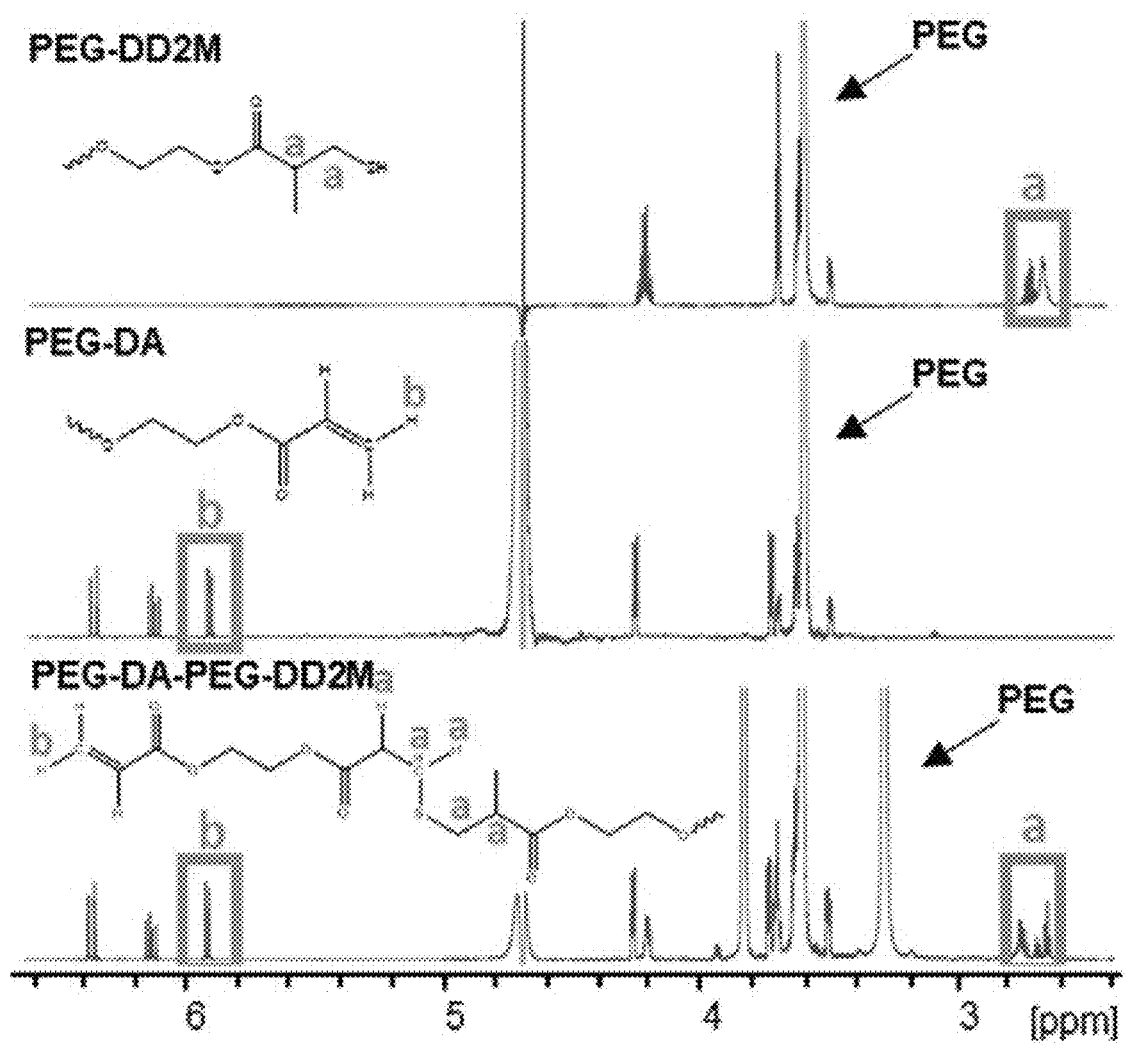
FIGS. 5A and 5B depicts acrylate consumption of hydrogels formed with PEG-DA and seven dithiol crosslinkers (3 Ac:1 SH) to determine the effect of hydrogel structure on reaction efficiency, as measured by $^1$H NMR. Representative spectra of $^1$H NMR of PEG-DD2M crosslinker (top), PEG-DA macromer (middle), and PEGDA-PEGDD2M polymer (bottom). The orange box at 5.83 ppm indicates the acrylate triplet peak used to measure acrylate consumption as compared to the PEG repeat unit at 3.52-3.62 ppm. The green box indicates the peaks at 2.54-2.83 ppm used to qualitatively determine that the PEG-DA-PEG-DD2M reaction had occurred (FIG. 5A). Relative percent acrylate consumption as measured by $^1$H NMR for hydrogels formed with seven dithiol crosslinkers. Lightly shaded bars represent aryl crosslinkers (FIG. 5B).
Figure 5B:
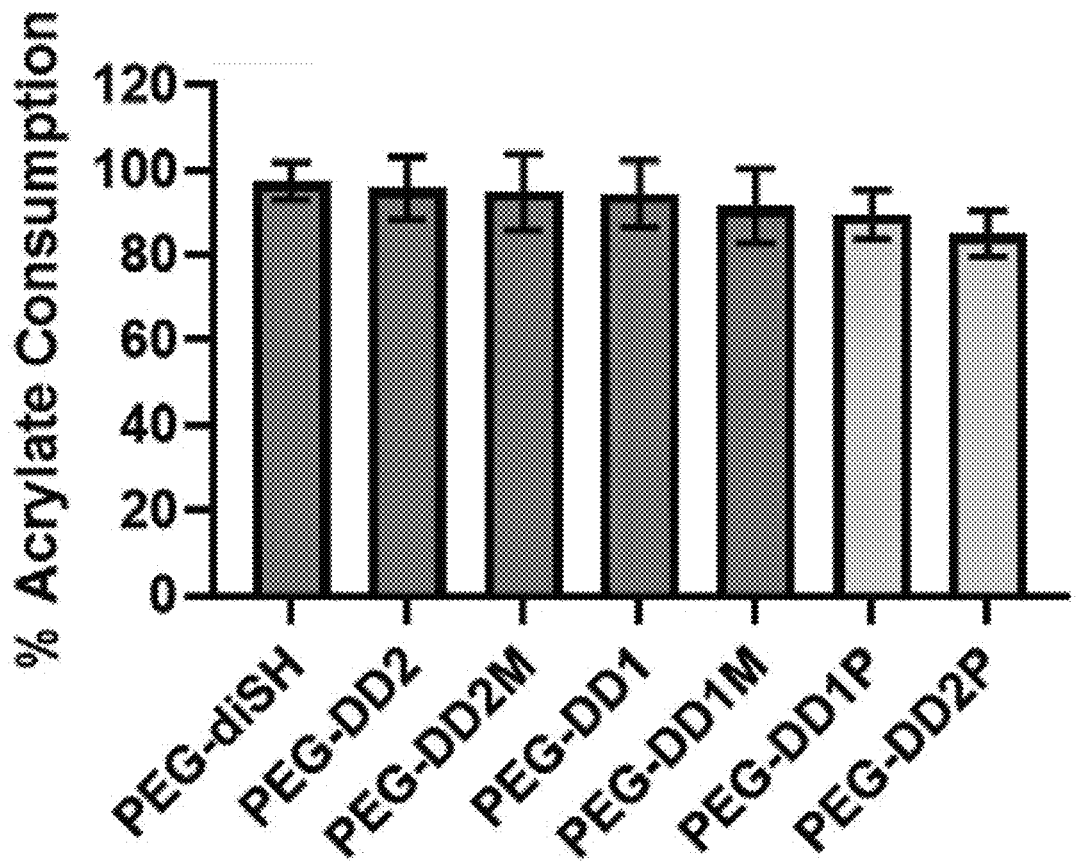

To determine reaction efficiency, thiol consumption was measured by Ellman's reagent (FIGS. 4A-4D) and acrylate consumption by $^1$H NMR (FIGS. 5A and 5B). The rate of thiol consumption varied from 0.3 to 4.8 $mM^{-1}$ $min^{-1}$ and corroborated gelation time data: faster gelation time corresponded to faster thiol consumption rate. Gels with PEG-DD2 and PEG-DD2M, which showed slower gelation, also showed slower thiol consumption of ~0.3 $mM^{-1}$ $min^{-1}$. Conversely, fast-gelling hydrogels made with PEG-DD1, PEG-DD1M, PEG-DD1P, and PEG-DD2P showed faster thiol consumption, 4.8, 1.0, 2.1, and 1.9 $mM^{-1}$ $min^{-1}$, respectively. Total thiol consumption ranged from 88 to 96%. The slow-gelling crosslinkers, PEG-diSH, PEG-DD2, and PEG-DD2M, had a maximum thiol consumption of ~96%. Conversely, the fast-gelling hydrogels showed lower levels of thiol consumption, with PEG-DD1, PEG-DD1M, PEG-DD1P, and PEG-DD2P showing thiol consumptions of 89%, 88%, 92%, and 93%, respectively.

For acrylate consumption measurements, the acrylate groups were at a 3-times molar excess to the thiol groups to avoid hydrogel formation. Hence, a 100% acrylate consumption was assumed if the ratios of one of the acrylate triplet peaks (5.83 ppm) to the PEG repeat unit (3.52-3.62 ppm) was ≥33.3%, signifying that ⅓ of the acrylate groups had been consumed. A representative $^1$H NMR spectra for PEG-DA (control), PEG-DD2M, and PEG-DA reacted with PEG-DD2M are shown in FIG. 5A. While the PEG-DD2M crosslinker showed two peaks at 2.83, these peaks were absent in the PEG-DA. However, the PEG-DA spectra included the addition of three acrylate peaks around 6 ppm; the peak at 5.83 (orange square) was used for consumption analysis. When the crosslinker reacted with the PEG-DA, the additional peaks at 2.83 (green square) indicated the two polymers had reacted. Total acrylate consumption is presented in FIG. 5B. PEG-diSH, PEG-DD2, PEG-DD2M showed almost complete acrylate consumption of ~96%. Again, the fast-gelling crosslinkers, namely PEG-DD1, PEG-DD1M, PEG-DD1P, and PEG-DD2P, showed lower, but not significantly different percent acrylate consumption of 94%, 92%, 90%, and 85%, respectively. In summary, the chemical structure of the crosslinkers had a minimal effect on their reaction efficiency.

Initial Swelling Ratio, Mesh Size, and Crosslink Density of PEG Hydrogels

Figure 6A:
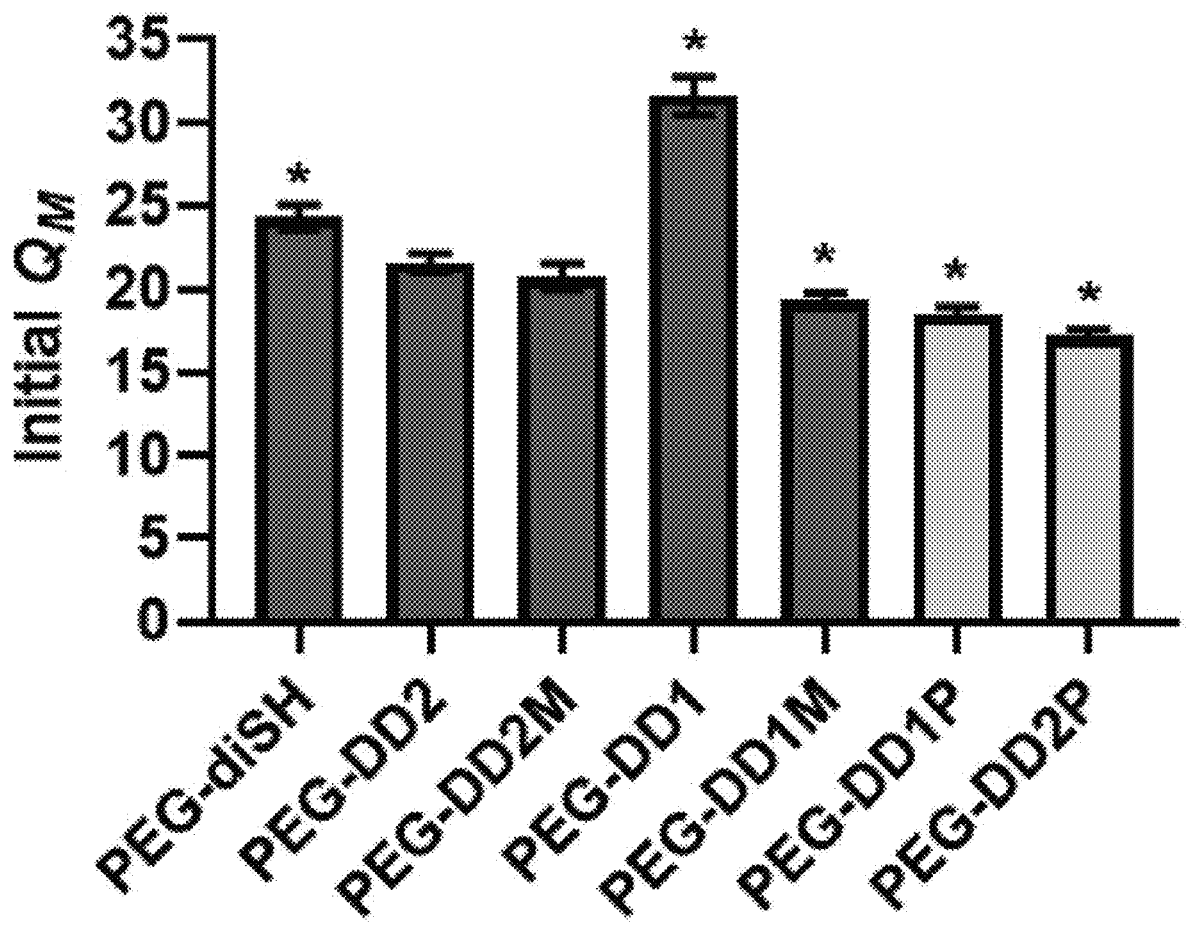
FIGS. 6A and 6B depicts initial swelling ($Q_M$) (FIG. 6A) and mesh size (f) (FIG. 6B) of hydrogels formed from 4-arm PEG-Ac crosslinked with seven dithiol crosslinkers. * indicates significance ($p<0.05$) between all groups and # indicates significance ($p<0.05$) between compared groups. Lightly shaded bars represent aryl crosslinkers.
Figure 6B:
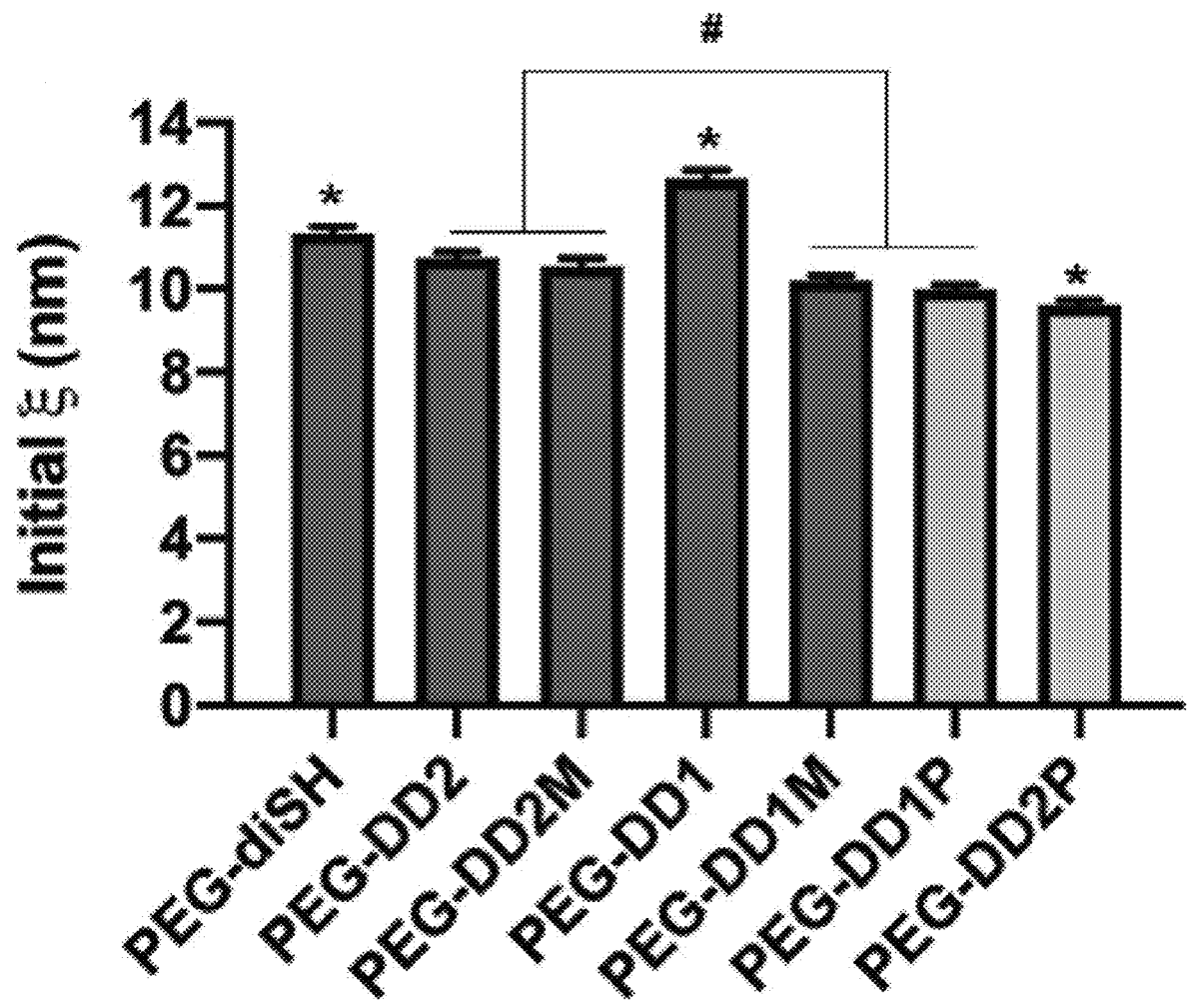

The effect of crosslinker chemical structure on the initial swelling ratio ($Q_M$), mesh size ($\xi$), and crosslink density ($v_c$) of hydrogels made with 4-arm PEG-Ac at pH 7.4 was examined (FIGS. 6A and 6B). Initial $Q_M$ ranged from 17 to 31 (FIG. 6A), which correlated with values from the literature. For example, $Q_M$ was reported to be ~19 for gels made with PEG-diSH and 4-arm PEG-Ac. All ester-containing crosslinkers, except for PEG-DD1, showed a significantly lower initial $Q_M$ than the non-ester containing PEG-diSH control. PEG-DD1 had a significantly higher $Q_M$ than PEG-diSH and all other crosslinkers. Without being bound by theory, this may be due to a complete mesh not forming, resulting in a highly swellable gel. $\xi$ was directly proportional to the $Q_M$ (FIG. 6B), where gels with higher $Q_M$ showed higher $\xi$. $\xi$ varied from 7-13 nm for all hydrogels, when gelation was conducted at a constant pH.

Crosslink density (Table 2) was inversely related to $Q_M$ and $\xi$, with a range of 0.17-0.56 mmol cm$^{-3}$. Gels with higher $Q_M$ and $\xi$ demonstrated lower crosslink density and gels with lower $Q_M$ and $\xi$ showed higher $v_c$. Gels crosslinked with PEG-DD1 showed lower $v_c$ than other gels. Percent deviation from ideal $v_c$ ranged from 76 to 93%, and was highest for the fast-gelling gels. Additionally, gels made with crosslinkers of similar chemical structures showed comparable deviation from ideal $v_c$, indicating $v_c$ was influenced by crosslinkers' chemical structure.

TABLE 2

Crosslink density ($v_c$) and percent deviation from ideal $v_c$ of hydrogels formed with the developed crosslinkers.

| Crosslinker | $v_c$ experimental (mmol cm$^{-3}$) | % Deviation from $v_c$ ideal (2.33 mmol cm$^{-3}$) |
|---|---|---|
| PEG-diSH | 0.28 | 87.8 |
| PEG-DD2 | 0.36 | 84.7 |
| PEG-DD2M | 0.39 | 83.3 |
| PEG-DD1 | 0.17 | 92.6 |
| PEG-DD1M | 0.44 | 81.0 |
| PEG-DD1P | 0.48 | 79.2 |
| PEG-DD2P | 0.56 | 75.9 |

Storage Modulus

Figure 7A:
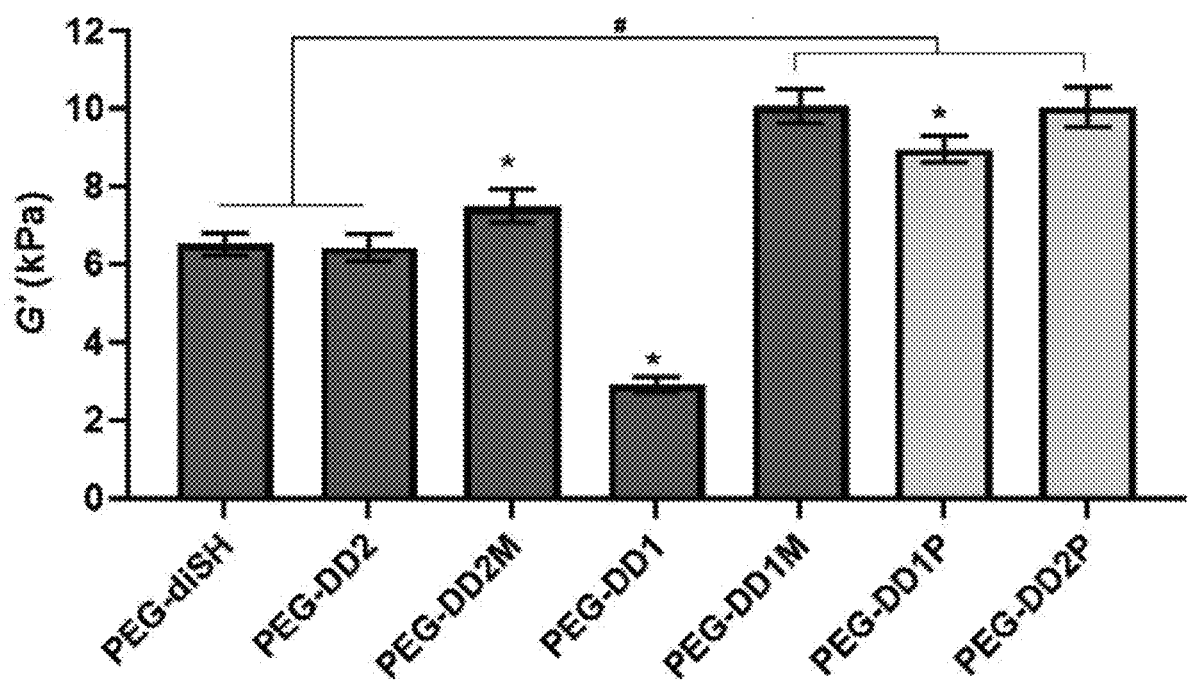
FIGS. 7A-7D depict rheological measurements of hydrogels formed with 4-arm PEG-Ac and seven dithiol crosslinkers to determine the effect of hydrogel structure on hydrogel viscoelasticity. Storage moduli (G') of all hydrogels made with indicated crosslinkers; data shown were collected at 1 Hz. Lightly shaded bars represent aryl crosslinkers. * indicates significance ($p<0.05$) between all groups and # indicates significance ($p<0.05$) between compared groups (FIG. 7A). Representative data for G' and G" as a function of angular frequency is shown for PEG-DD1 (FIG. 7B). Representative data for G' and G" as a function of angular frequency is shown for PEG-DD1P (FIG. 7C). Lines are provided in FIGS. 7B and 7C to guide the eye. Correlation between initial G' and gelation time (FIG. 7D).
Figure 7B:
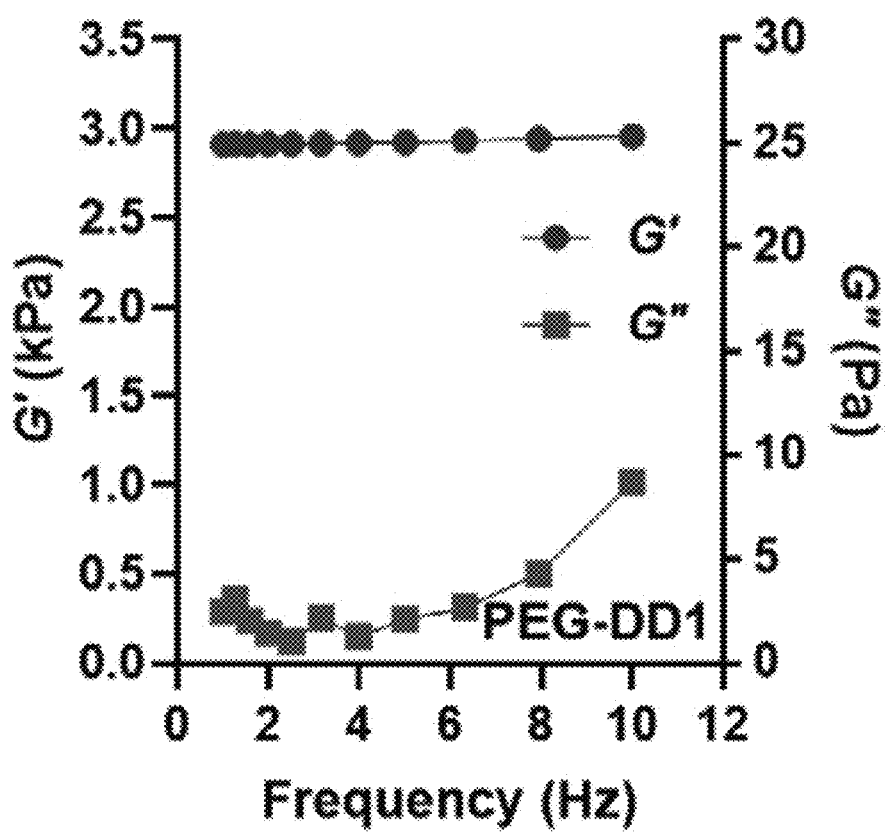
Figure 7C:
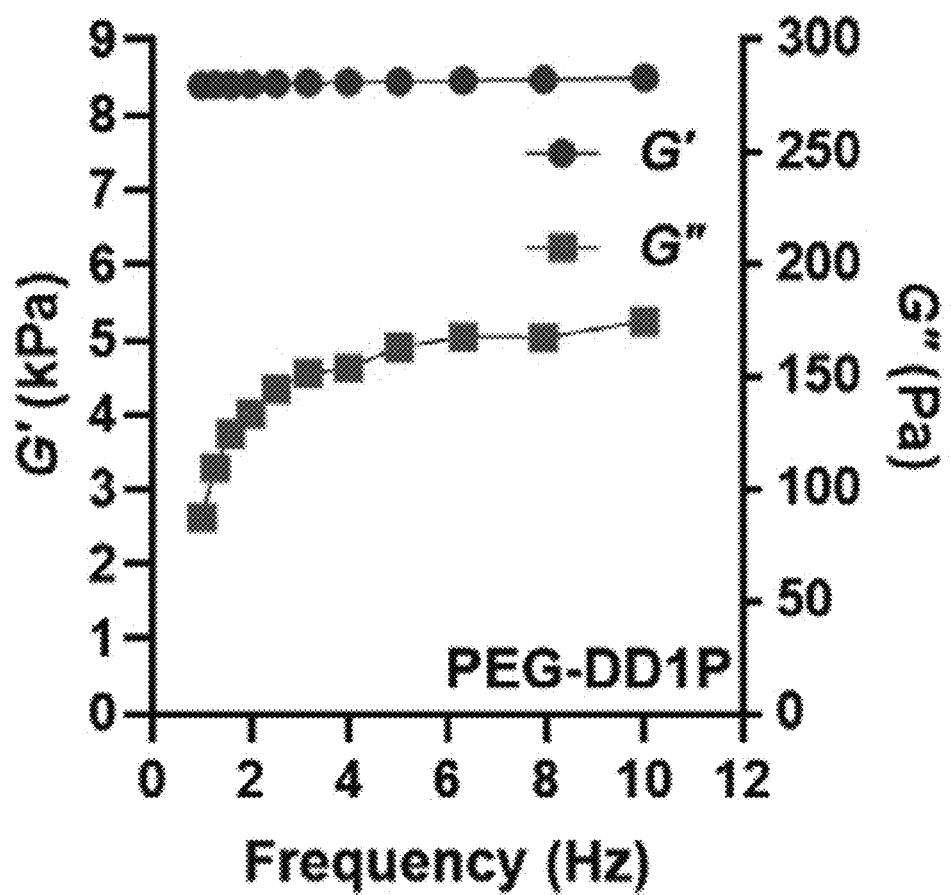
Figure 7D:
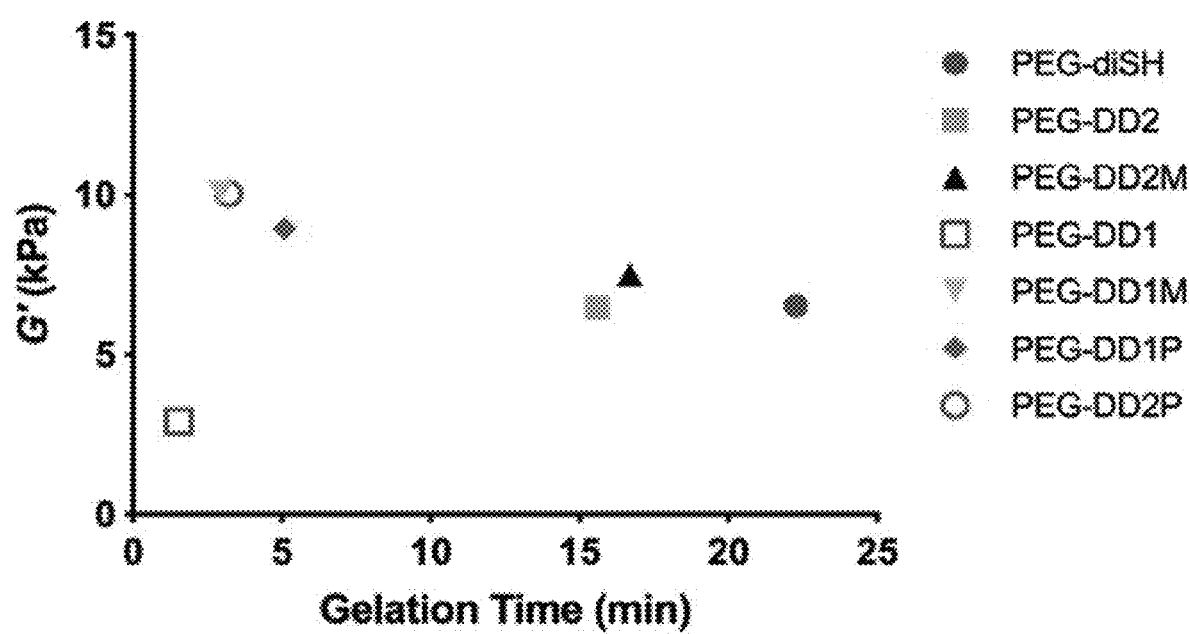
Figure 8A:
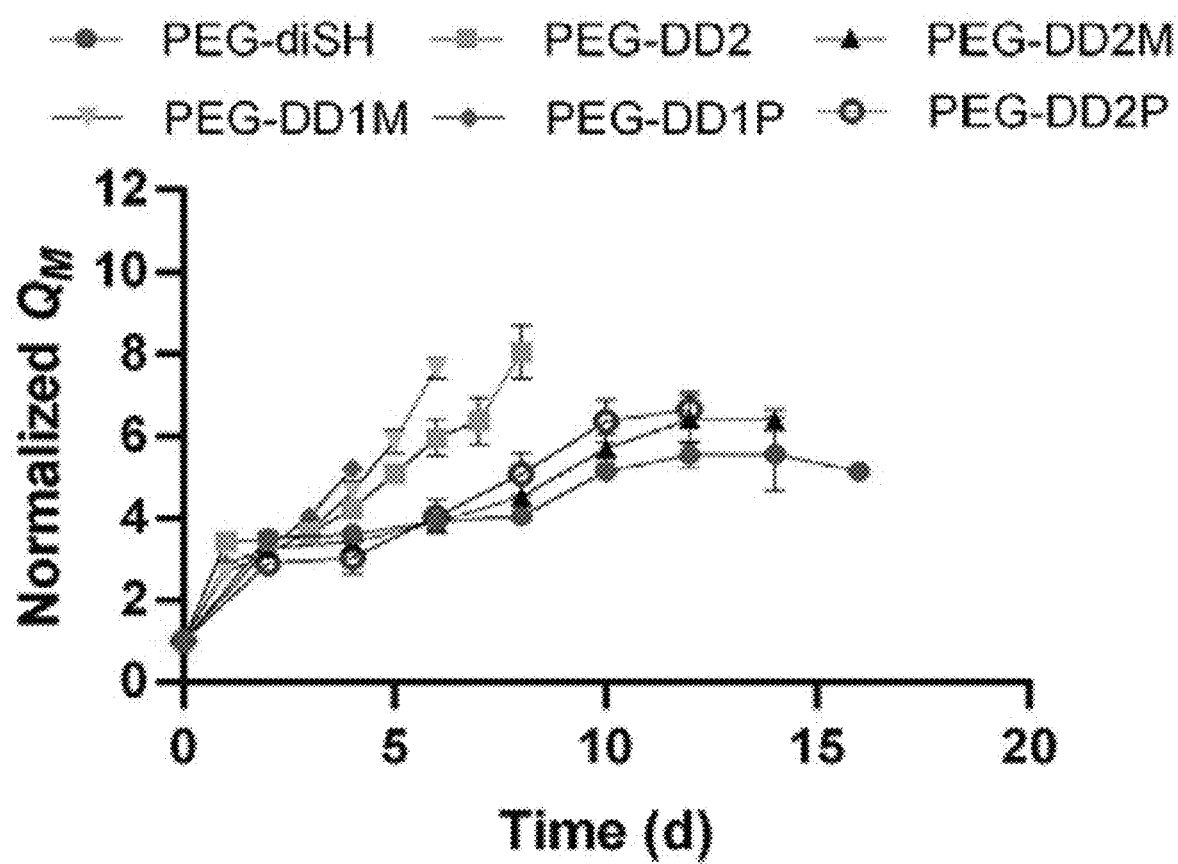
FIGS. 8A-8D depict degradation of hydrogels formed with 4-arm PEG-Ac and seven dithiol crosslinkers to determine the effect of crosslinker structure on degradation. Normalized $Q_M$ over time until complete degradation (FIG. 8A). Normalized $Q_M$ over time until complete degradation for PEG-DD1 (FIG. 8B). Degradation time of hydrogels formed with seven dithiol crosslinkers (FIG. 8C). Degradation rate of hydrogels formed with seven dithiol crosslinkers (FIG. 8D). Lightly shaded bars represent aryl crosslinkers. * indicates significance ($p<0.05$) between all groups and # indicates significance ($p<0.05$) between compared groups.
Figure 8B:
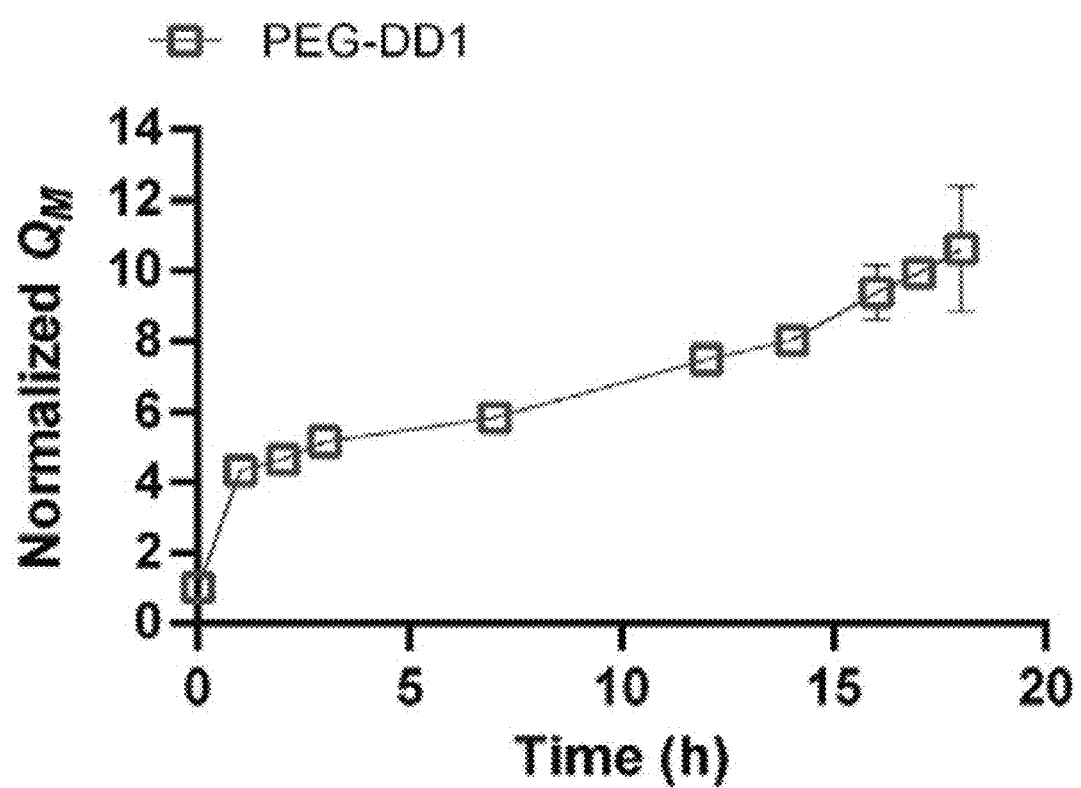
Figure 8C:
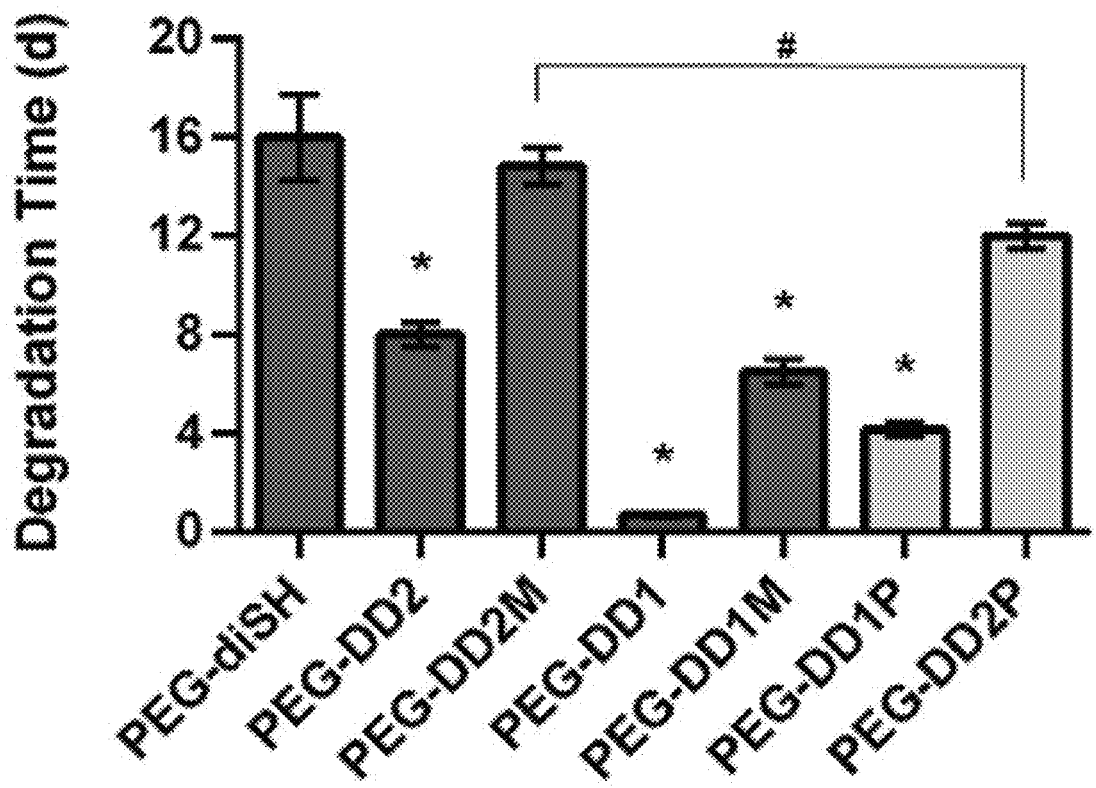
Figure 8D:
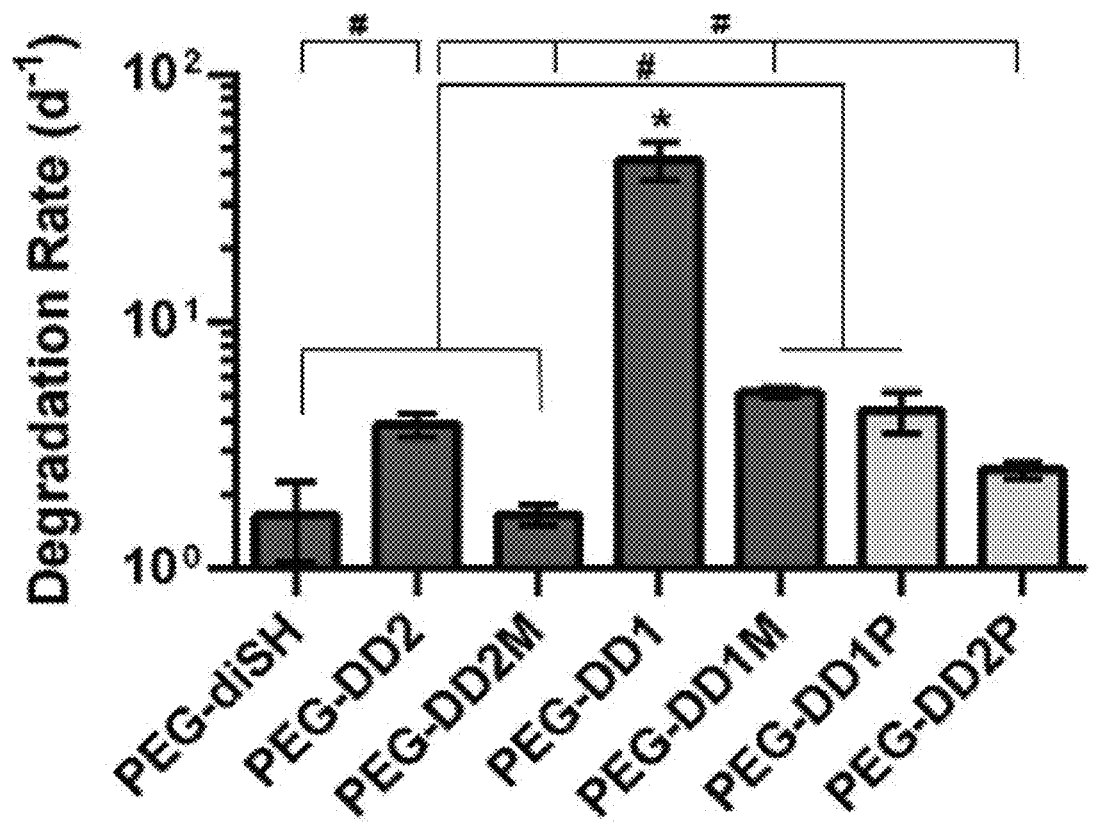

Initial storage modulus (G') ranged from 3 to 10 kPa for all gels tested (FIG. 7A). Representative data on G' and G" as a function of frequency for PEG-DD1 and PEG-DD1P is shown in FIG. 7B. The data indicate that the moduli were mostly independent of frequency (for a low frequency range) and that G' was orders of magnitude higher than G", underscoring the viscoelastic nature of the developed gels. Generally, G' was inversely related to initial $Q_M$ and $\xi$, where gels with higher initial $Q_M$ showed lower G'. These data corroborated the hypothesis that a smaller $\xi$ results in gels of higher moduli due to their ability to resist motion more readily than those of larger $\xi$. Further, crosslinker chemical structure influenced G', when gels were formed at a constant pH. Increased hydrophobicity between the thiol and the ester resulted in a higher G' as in PEG-DD1 vs. PEG-DD2, PEG-DD2 vs. PEG-DD2M, PEG-DD1 vs. PEG-DD1M, and PEG-DD1P vs. PEG-DD2P. Notably, gels made with PEG-DD1 presented relatively low G' of 2.9 kPa, which may be a result of a combination of the terminal thiol $pK_a$ during gelation and the hydrophilicity of the crosslinker.

Hydrogel Degradation Measured by Swelling

Degradation was measured indirectly by following the change in $Q_M$ over time. Gels made with the synthesized ester-containing crosslinkers degraded more quickly than those crosslinked with the non-ester-containing crosslinker, PEG-diSH, with degradation times ranging from 18 hours to 16 days (FIGS. 8A-8D). Gels made with PEG-DD1 degraded most quickly. Comparatively, gels made with PEG-DD1M took longer to degrade due to increased steric hindrance and hydrophobicity caused by the additional methyl group in the ester vicinity. A similar observation was made for gels formed with the crosslinkers PEG-DD2 vs. PEG-DD2M. Conversely, the degradation rates of PEG-DD1P and PEG-DD2P were slightly reduced compared to PEG-DD1M and PEG-DD2M, respectively. Without being bound by theory, it is believed that this may be due to the electron-withdrawing phenyl group near the ester moiety.

Adjustment of Reaction pH to Account for Rate of Thiol Deprotonation

For all characterizations above, a single reaction pH was used for consistency. To determine the effect of pH on gelation time, the reaction pH was adjusted for the following crosslinkers: PEG-DD1 (pH 6.25), PEG-DD1P and PEG-DD2P (pH 6.2). By decreasing the reaction pH, a gelation time of ~15 minutes for all three crosslinkers was achieved, which was similar to the gelation time of PEG-DD2. The slow-gelling PEG-DD2 was used for comparison. Similar gelation times resulted in similar initial properties, including $Q_M$, $\xi$, and $v_c$ (Table 3). While degradation times were also affected by reaction pH, the change was minimal. Degradation time of gels crosslinked with PEG-DD1 increased from 18 hours to 28 hours, and gels made with PEG-DD1P and PEG-DD2P increased from 6 days and 12 days to ~7 days and 13 days, respectively. Overall, these results showed that when thiol deprotonation rate was standardized, hydrogels made with crosslinkers of different moieties near the ester have similar initial properties, but different degradation times.

TABLE 3

Initial properties and degradation times of hydrogels made with the developed crosslinkers at different pH, chosen to account for the rate of thiol deprotonation. PEG-DD2 hydrogels prepared at pH 7.4 are shown for comparison.

| Cross-linker | Reaction pH | Gelation Time (min) | Initial $Q_M$ | Initial $\xi$ (nm) | $v_e$ (mmol/cm³) | Degradation Time (d) |
|---|---|---|---|---|---|---|
| PEG-DD2 | 7.4 | 15.7 ± 0.6 | 21.6 ± 0.6 | 8.7 ± 0.3 | 3.5 ± 0.2 | 8.0 ± 0.5 |
| PEG-DD1 | 6.25 | 15.8 ± 1.0 ↑↑↑ | 24.1 ± 2.5 ↓ | 9.8 ± 1.0 ↓ | 1.9 ± 0.4 ↑ | 1.2 ± 0.2 ↑ |
| PEG-DD1P | 6.2 | 16.6 ± 1.2 ↑↑ | 22.5 ± 1.7 ↑ | 9.2 ± 0.8 ↑ | 2.1 ± 0.4 ↓ | 6.8 ± 0.9 ↑ |
| PEG-DD2P | 6.2 | 14.1 ± 1.2 ↑↑ | 19.7 ± 1.5 ↑ | 7.9 ± 1.1 ↑ | 3.1 ± 0.8 ↓ | 13.5 ± 0.7 ↑ |

↑ indicates 1 to 5-fold change,
↑↑ indicates 6 to 9-fold change, and
↑↑↑ indicates ≥ 10-fold change from hydrogels made with the same crosslinker at pH 7.4.

Figure 9A:
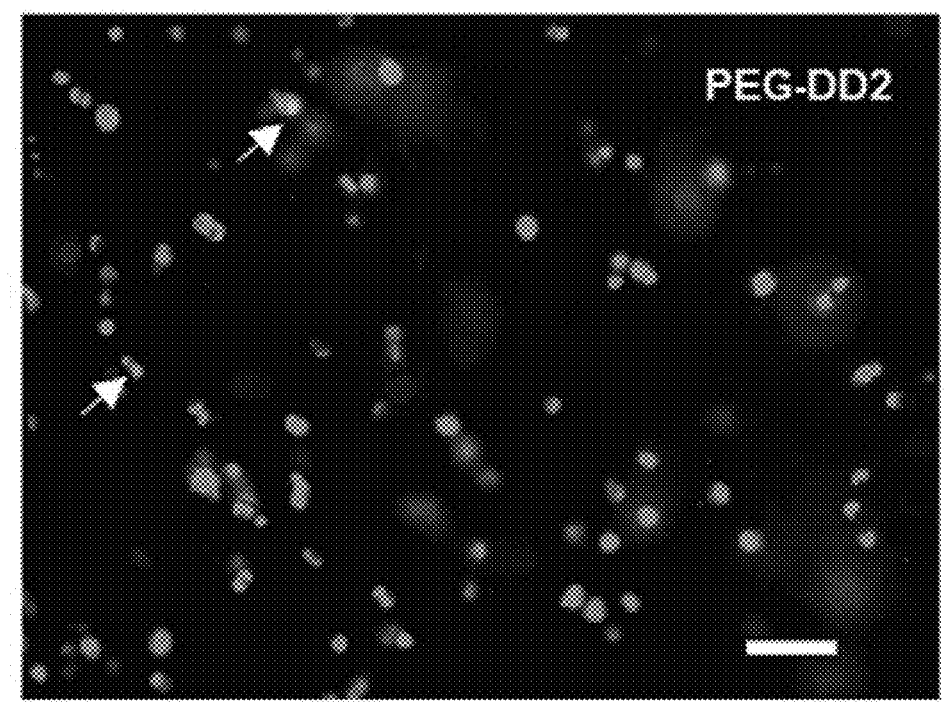
FIGS. 9A-9D depict cell viability measurements of hydrogels formed with 4-arm PEG-Ac and seven dithiol crosslinkers to determine the effect of hydrogel structure on cell viability. Image of U87 cells encapsulated in hydrogel crosslinked with PEG-DD2 at 48 hours (FIG. 9A). Scale bar represents 100 μm. Percent viability of U87 cells encapsulated in hydrogels made with the respective crosslinkers and cultured for 48 hours (FIG. 9B). Schematic of hydrogel leachable experiment (FIG. 9C). Percent viability of U87 cells exposed for 48 hours to leachables (collected at 24 hours, 48 hours and complete degradation) from hydrogels made with the respective crosslinkers (FIG. 9D). All hydrogels and their degradation products were cytocompatible. Lightly shaded bars represent aryl crosslinkers.
Figure 9B:
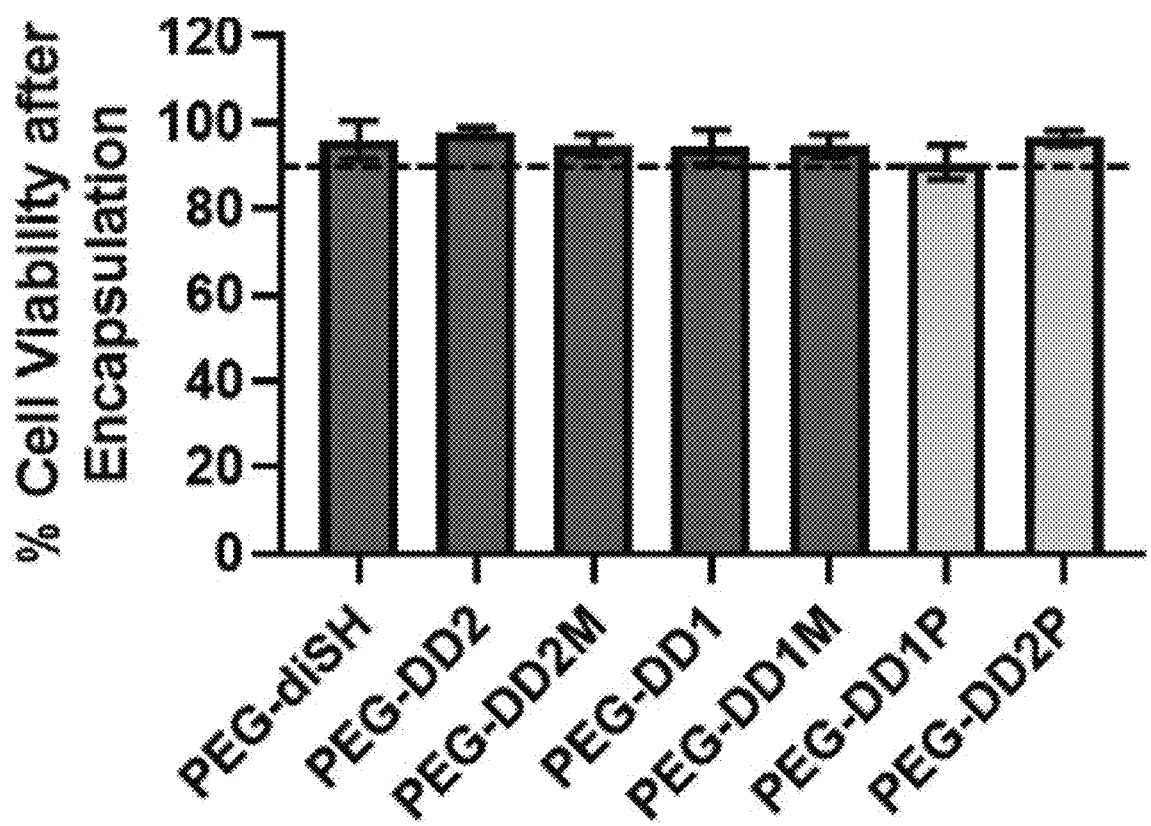
Figure 9C:
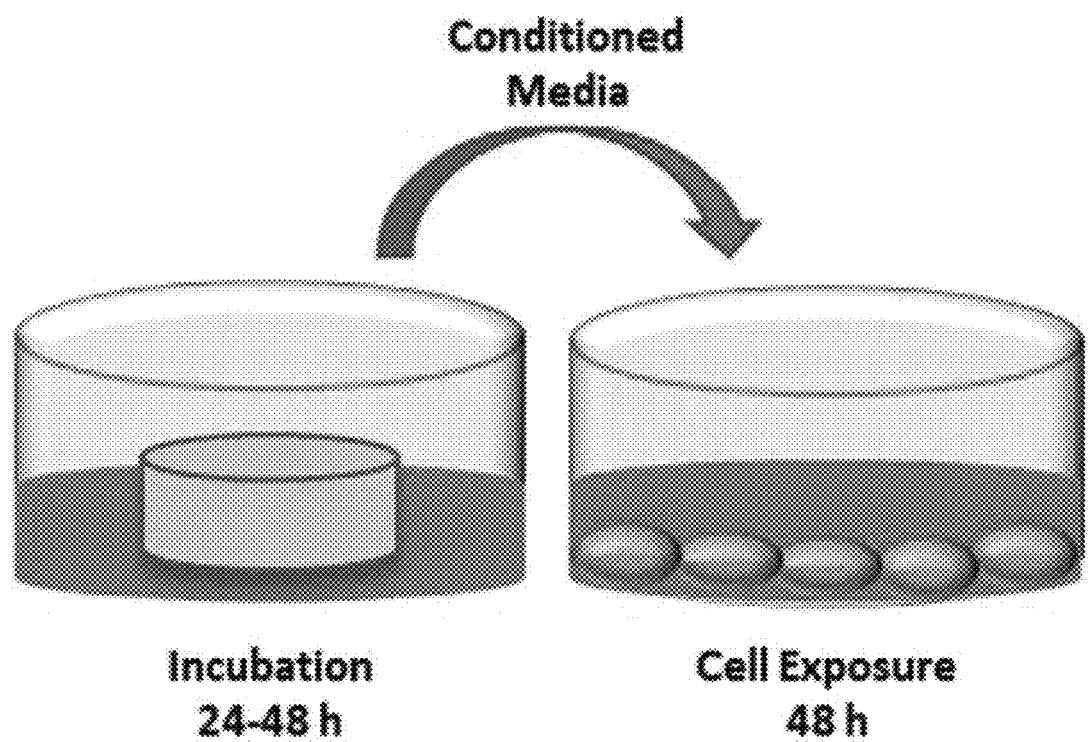
Figure 9D:
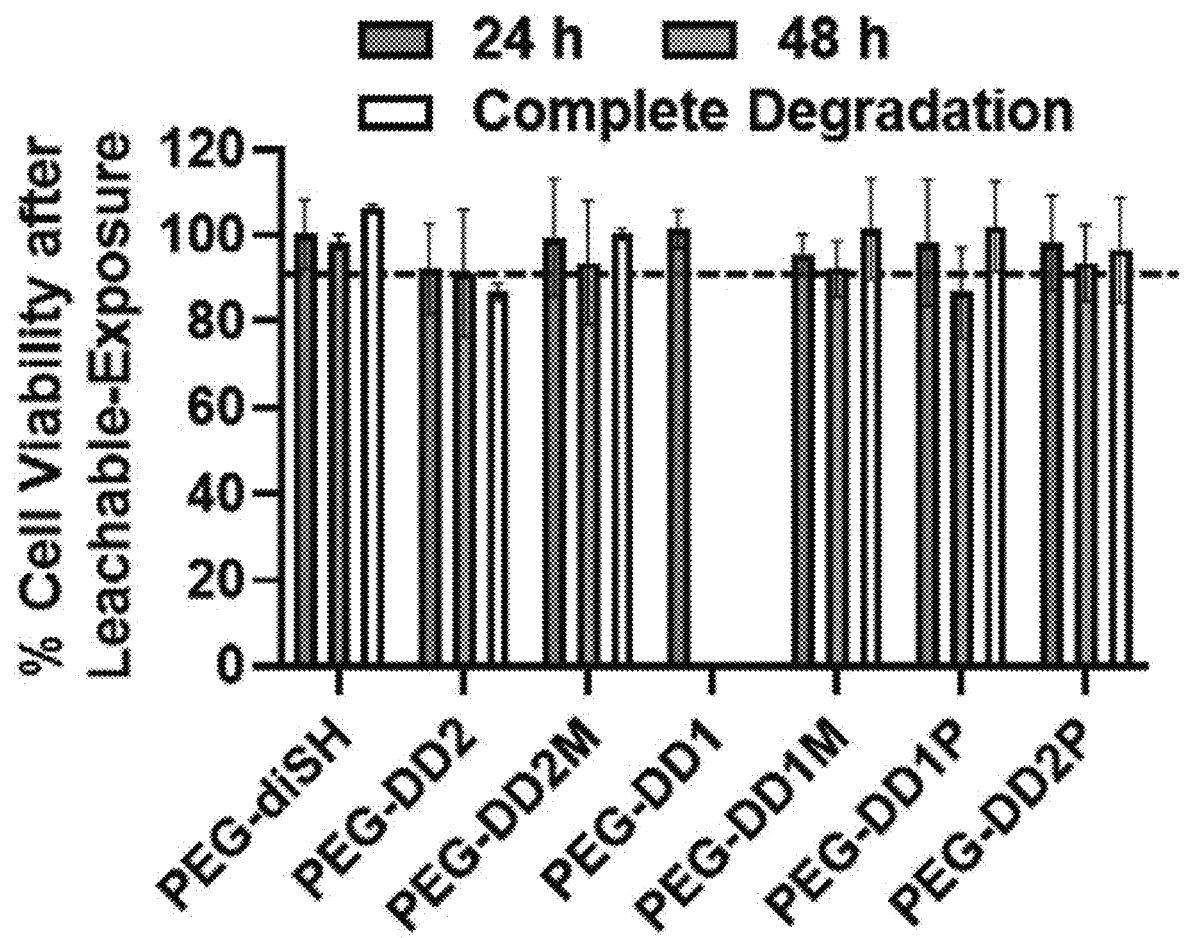

Crosslinker Cytotoxicity: Hydrogel Encapsulation, Leachables, Degradation Products Cytotoxicity of the synthesized crosslinkers was determined in two separate experiments: by directly encapsulating cells during gel formation and by exposing cells to leachables and degradation products. Gels made with the commercially available PEG-diSH crosslinker were used as a control. At least 90% of U87 cells remained viable 48 hours after encapsulation in gels made with the 6 synthesized crosslinkers (FIGS. 9A and 9B). The cytotoxicity of leachables at 24 hours and 48 hours, and at gel degradation (FIGS. 9C and 9D) was also determined. Cells showed ~90% viability for all gel types after exposure to leachables from all three time points: 24 hours, 48 hours, and complete degradation. Because gels crosslinked with PEG-DD1 degraded in <24 hours, the cell viability after 24 hours degradation was equivalent to cell viability after complete degradation (only the 24-hour data is shown). These data indicate that the developed crosslinkers as well as the resulting hydrogels were cytocompatible and also compatible with direct cell encapsulation.

These Examples present a library of hydrolytically degradable and chemically distinct PEG-based crosslinkers, which result in hydrogels with diverse degradation times. PEG hydrogels were prepared by a conjugate addition reaction between 4-arm PEG-Ac and the synthesized PEG-diester-dithiol crosslinkers. This conjugate addition occurs between a thiolate ion (a deprotonated thiol) and an α-β unsaturated ester as in an acrylate or vinyl sulfone group. This reaction mechanism is advantageous because it is a mild, highly specific reaction that can occur at physiologically relevant conditions, and ultimately form reproducible networks via step-wise polymerization. Acrylate end-functionalized PEG, when reacted via conjugate addition, forms a thioether-ester bond. While the ester bond in unreacted PEG-acrylate is only slightly hydrolytically degradable, the proximity of the thioether group to the PEG-acrylate ester increases the sensitivity of that ester to hydrolytic degradation by several orders of magnitude. This leads to cleavage of the modified ester and the breakdown of the crosslinked network on time periods appropriate for many drug delivery and tissue engineering applications.

To achieve tunable hydrogel properties, crosslinkers were designed with hydrolytically degradable moieties, namely ester bonds. Ester hydrolysis occurs via nucleophilic attack of the carbonyl carbon by hydronium ions and is influenced by chemical moieties near the ester. For example, hydrophobic groups near the ester diminish water access and resist nucleophilic attack from occurring readily. Also, chemical moieties that withdraw from or donate electrons to the carbonyl carbon influenced its nucleophilicity and further affected hydrolysis. Thus, the strategy was to modulate degradation by varying the chemical moieties in the ester vicinity. This was accomplished by incorporating methylene spacers between the ester and the thiol (hydrophobicity), methyl pendant groups (hydrophobicity and steric hindrance), and phenyl groups between the ester and thiol (electron withdrawing). Increasing the number of methylene spacers slowed degradation by increasing hydrophobicity near the ester and also by diminishing the influence of the electron-withdrawing thiol group. Additionally, methyl pendant groups further increased hydrophobicity and provided steric hindrance near the ester, slowing degradation. Finally, incorporating phenyl groups accelerated degradation by withdrawing electrons and making the carbonyl carbon a better nucleophile. These strategies resulted in degradation times ranging from 18 hours to 16 days. Additional strategies, such as using a multi-arm PEG-vinyl sulfone as opposed to PEG-acrylate or changing polymer molecular weight and concentration, can result in further changes in degradation time, underscoring the flexibility of the chosen approach. The developed hydrogels showed degradation time ranges similar to other available PEG hydrogels. For example, PEG-diacrylate hydrogels formed by conjugate addition with DTT had degradation times of up to 21 days, and PEG-PLA with increasing numbers of lactoyl units had times of 4 days to 17 days.

To determine whether modulating the crosslinker chemical structure would change initial hydrogel physical and mechanical properties, extensive characterizations were performed. It was believed that changes in the chemical structure near the thiol would change thiol $pK_a$ (Table 1) and gelation time. When manipulating the crosslinker chemical structures but keeping a constant reaction pH of 7.4, gelation times were either fast (≤5 minutes) or slow (≥14 minutes) (FIG. 3). These differences can be explained by looking at how the reaction promotes deprotonation of the thiol group, resulting in a thiolate ion. The formation of the thiolate is controlled by the pH of the surrounding solvent and the inductive effects of chemical moieties near the terminal thiol, which modulate its $pK_a$. For example, the crosslinker PEG-DD1 has only one methylene spacer between the ester and the thiol moieties. This shifted the electron cloud toward the thiol, increasing its electronegativity and allowing it to easily lose a proton and form the thiolate ion. Overall, for a set reaction pH, thiols with a lower $pK_a$ can more easily lose a proton, leading to faster gelation than thiols with higher $pK_a$. The Examples showed that the crosslinkers with a thiol $pK_a$<9 had quick gelation (Table 1), which is corroborated by other studies where the threshold between slow- and fast-gelling crosslinkers $pK_a$ was determined to be ~8.5-8.7. As previously discussed, thiol $pK_a$ was influenced by neighboring groups. For instance, PEG-DD1 had a $pK_a$ of ~7.9-8.1 due to the proximity of the ester and the thiol. This allowed it to become a better electron acceptor and therefore to more easily form thiolate ions. Further separation of the thiol from the ester, as in PEG-DD2 ($pK_a$~9.4-9.6) stabilized the thiol and reduced its ability to form the thiolate ion, slowing gelation. In summary, the gelation times of the designed crosslinkers resulted from the $pK_a$ of the terminal thiol, which was modulated by the substituent groups near the thiol and aryl versus alkyl thiols.

Next, the reaction efficiency and reaction kinetics werer analyzed by measuring thiol and acrylate consumption upon reaction completion (FIGS. 4 and 5). Reaction efficiency is affected by molecule (in this case crosslinker thiol) $pK_a$, which is influenced by chemical groups near the thiol. Ideally, a complete reaction between the acrylate and thiolate is observed. This would indicate that a complete meshwork can be formed between the PEG macromer and the crosslinker, leading to similar hydrogel mechanical properties. Experiments were performed with a 3-fold molar excess of Ac to SH to observe the inherent reaction efficiency of the crosslinkers independent of crosslinked network formation. When a network is formed, not all available end groups can react due to decreased mobility and range upon gelation. Hence, although all crosslinkers may have a high reaction efficiency, that may not result in a high crosslinking efficiency and formation of an ideal network (as seen in Table 2). Rather, gelation time and rate of thiol deprotonation affect network formation, giving gels formed with different crosslinkers different initial properties (when not controlled for rate of thiol deprotonation). For example, PEG-DD1 had a high reaction rate and reaction efficiency but presented a non-ideal network.

Alkyl crosslinkers with two methylene spacers between the ester and the thiol, such as PEG-DD2 and PEG-DD2M, consumed thiol at rates similar to the non-ester-containing crosslinker, PEG-diSH. Further, crosslinkers of similar structures could be grouped according to their reaction efficiency, such as PEG-DD2 and PEG-DD2M, PEG-DD1 and PEG-DD1M, or PEG-DD1P and PEG-DD2P. This fits with other findings that crosslinkers of similar chemical structure show minor differences in reaction efficiency. The aryl crosslinkers PEG-DD1P and PEG-DD2P also had higher thiol consumption rates than the alkyl crosslinkers (excluding PEG-DD1), which could be due to the influence of the phenyl group; the phenyl group near the thiol lowered the thiol $pK_a$ (Table 1), increasing thiol consumption. Acrylate consumption followed trends similar to those observed in the thiol consumption data. These results indicated almost complete acrylate and thiol consumption independent of the crosslinker chemical structure and reactivity, signifying that different degradation rates were not linked to reaction efficiency alone.

Initial physical properties of hydrogels, namely, $Q_M$, $\xi$, $v_c$, and G' were then analyzed (FIGS. 6 and 7). While most crosslinkers formed gels with somewhat similar properties, gels crosslinked with PEG-DD1 were notable outliers. It should be noted that $Q_M$ and $\xi$ are inversely proportional to $v_c$ and G'. While significant differences were observed between all gels, the range of initial properties was still relatively narrow (excluding PEG-DD1). These differences could be due to the differences in the crosslinkers' inherent hydrophobicity. Hydrogels made with PEG-DD1 presented a very high $Q_M$ (31.6) and $\xi$ (12.5 nm) and low $v_c$ (0.173 mmol cm$^{-3}$) and G' (2.9 kPa) compared to all other gels. This may be caused by the low thiol $pK_a$ and rapid gelation of PEG-DD1 (90 seconds) leading to an incomplete network, as supported by the data presented above, allowing increased water influx into the hydrogel.

Chemical structure of the crosslinkers affected hydrogel degradation. Gels made with ester-containing crosslinkers degraded faster than gels made with the non-ester-containing control crosslinker, PEG-diSH. Hydrolysis can be controlled by affecting the stability of the carbonyl carbon or restricting water access to it. Degradation was influenced by the methylene spacers between the ester and the thiol and the identity of the chemical moieties near the ester. A shorter spacer between the ester and thiol groups increased thiol acidity and made the ester more susceptible to nucleophilic attack. Conversely, greater distance between the two groups increased hydrophobicity and stability of the ester, reducing its liability to nucleophilic attack and slowing degradation. These concepts are seen in the following comparisons. Gels made with crosslinkers with shorter methylene spacers between the thiol and ester (e.g. PEG-DD1, PEG-DD1M, PEG-DD1P) degraded faster than those made with crosslinkers with longer spacers between the thiol and the ester, but otherwise similar structures (e.g. PEG-DD2, PEG-DD2M, PEG-DD2P). Incorporating methyl groups further increased hydrophobicity and possibly steric hindrance, further slowing degradation. For instance, gels made with crosslinkers containing additional hydrophobic methyl groups, PEG-DD1M and PEG-DD2M, degraded more slowly than those not containing pendant groups between the ester and thiol—PEG-DD1 and PEG-DD2, respectively. Further, destabilization of the carbonyl carbon was introduced by incorporating an electronegative phenyl group between the ester and thiol into PEG-DD1P and PEG-DD2P. PEG-DD1P showed significantly faster degradation than PEG-DD2. However, PEG-DD2P degraded in a relatively long time of ~12 days. Without being bound by theory, this could be affected by an increase in hydrophobicity in PEG-DD2P, which increased stability and slowed degradation. These data show that the hydrogels made with the developed crosslinkers showed varied degradation due to differing chemical structures.

Trends were also observed between gelation and degradation time; the fast-gelling gels were fast-degrading, and the slow-gelling gels were slow-degrading. Gels made with PEG-DD2P were the exception; though fast-gelling (3 minutes), these were slow-degrading (12 days). This may be due to the large distance between the phenyl and ester groups. The high electronegativity of the phenyl group sped gelation. However, the greater distance between the phenyl and ester, as compared to PEG-DD1P, decreased the phenyl group influence on degradation. Rather, the ester was stabilized by the methylene groups, slowing degradation.

The ability to maintain similar mechanical and physical properties, while varying gel degradation times was also analyzed. Because gels crosslinked with PEG-DD1 showed significantly different initial properties than those made with other crosslinkers, whether changing the reaction pH in accordance with the thiol $pK_a$ would alter the initial properties by reducing the thiol deprotonation rate was determined (Table 3). By the Henderson-Hasselbalch equation, it was determined that at a reaction pH of 7.4, ~25% of the PEG-DD1 thiols were deprotonated and able to interact with PEG-Ac. By reducing the reaction pH to 6.25, the deprotonated thiols decreased to ~1.8%. This value correlated with the percentage of deprotonated thiols (~0.8%) in PEG-DD2 at pH 7.4. Consequently, the gelation time increased to 15.8 minutes, which also affected the crosslinked network, as seen in the decreased initial $Q_M$ and $\xi$, and the increased $v_c$ to values closer to gels made with the other alkyl crosslinkers. Further, while still short, degradation time increased to >24 hours, which correlated with a tighter $\xi$ and higher $v_c$.

Also, the differences in alkyl versus aryl thiols lead to different gel properties. Due to the presence of the phenyl groups, the aryl crosslinkers (PEG-DD1P and PEG-DD2P)

are inherently more hydrophobic than the alkyl crosslinkers. Further, the alkyl thiols reacted faster than the aryl thiols once deprotonated because of their inherent nucleophilicity. However, this depended on the crosslinkers' deprotonation rate, and as the thiol consumption data show, the aryl crosslinkers deprotonate more quickly than the alkyl crosslinkers. Because the $pK_a$ of the aryl crosslinkers is ≤7, and they react so quickly, how reducing the reaction pH (and thus increasing gelation time) would affect network formation was analyzed. This also slightly affected gels' initial properties and slowed degradation. These results show that the initial properties could be maintained, while affecting degradation time, by modulating the gels' reaction pH. Overall, final gel properties depended on the reaction kinetics. Finally, by adjusting the reaction pH in accordance with the crosslinker thiol $pK_a$, the desired gel properties were achieved, and changing only the crosslinker changed degradation time without significantly affecting the initial properties.

Lastly, biocompatibility of gels made with the designed crosslinkers was analyzed. U87 cells survived encapsulation in gels made with all crosslinkers. Moreover, the gel leachables and degradation products were found to be non-cytotoxic to cells exposed to the gel leachables and degradation products. The developed gels were biocompatible and hydrophilic, permitting biomedical applications including drug delivery systems, as substrates for basic biological research, as matrices for cell encapsulation and transplantation, and as in vitro models for drug screening.

Degradable PEG-based crosslinkers with distinct chemical structures were synthesized and demonstrated tuning of degradation rates by modulating crosslinkers' chemical structure. Altering chemical moieties near the ester achieved a range of degradation times appropriate for biomedical applications. Finally, all developed crosslinkers supported high cell viability during encapsulation and exposure to hydrogel leachables and degradation products.

Crosslinkers of the present disclosure provide degradation times of hydrogels prepared using the crosslinkers ranging from hours to weeks due to differing chemical structures, particularly the moieties between the ester and thiol groups. Longer degradation rates are achieved using crosslinkers with longer carbohydrate chain length and steric hinderance, whereas using electron-withdrawing groups provides hydrogels with accelerated degradation rates. Change in degradation is coupled to gelation time: fast-gelling hydrogels were also fast-degrading and slow-gelling hydrogels were also slow-degrading.

What is claimed is:

1. A hydrogel crosslinker of formula (I),

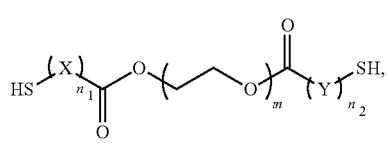

wherein m is at least 10 repeating units; $n_1$ and $n_2$ ranges from 1 to 5 repeating units; X and Y are independently selected from $CHR^1$, $NR^2$, O, $SR^3$, and aryl; $R^1$ is selected from alkyl, alkoxy, aryl, hydroxyl, amino, nitro, carboxyl, a halogen, a polar pendant group, and a non-polar pendant group; and $R^2$, and $R^3$ are independently selected from H, alkyl, alkoxy, aryl, hydroxyl, amino, nitro, carboxyl, a halogen, a polar pendant group, and a non-polar pendant group.

2. A hydrolytically degradable hydrogel comprising a crosslinker of formula (I),

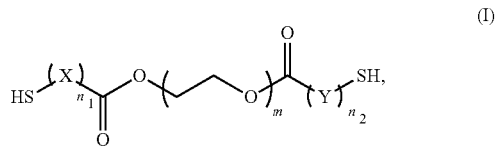

wherein m is at least 10 repeating units; $n_1$ and $n_2$ ranges from 1 to 5 repeating units; X and Y are independently selected from $CHR^1$, $NR^2$, O, $SR^3$, and aryl; $R^1$ is selected from alkyl, alkoxy, aryl, hydroxyl, amino, nitro, carboxyl, a halogen, a polar pendant group, and a non-polar pendant group; and $R^2$, and $R^3$ are independently selected from H, alkyl, alkoxy, aryl, hydroxyl, amino, nitro, carboxyl, a halogen, a polar pendant group, and a non-polar pendant group; and a polymer.

3. The hydrolytically degradable hydrogel of claim 2, wherein the polymer comprises poly(enthylene glycol)-di-acrylate (PEG-DA), multi-arm poly(ethylene glycol)-acrylate (PEG-Ac), poly(ethylene glycol)-dithiol (PEG-diSH), poly(ethylene glycol) divinyl sulfone (PEG-diVS), multi-arm poly(ethylene glycol) vinyl sulfone (PEG-VS), poly(enthylene glycol)-di-methacrylate (PEG-DMA), multi-arm poly(ethylene glycol)-methacrylate (PEG-MAc), poly(ethylene glycol)-di-allyl ether (PEG-diAE), multi-arm poly(ethylene glycol)-allyl ether (PEG-AE), poly(ethylene glycol)-di-vinyl ether (PEG-diVE), multi-arm poly(ethylene glycol)-vinyl ether (PEG-VE), poly(ethylene glycol)-di-maleimide (PEG-diMI), multi-arm poly(ethylene glycol)-maleimide (PEG-MI), poly(ethylene glycol)-di-norborene, multi-arm poly(ethylene glycol)-norborene, poly(ethylene glycol)-di-vinyl carbonate, multi-arm poly(ethylene glycol)-vinyl carbonate, polyethylene glycol oligofumarate, and combinations thereof.

4. The hydrolytically degradable hydrogel of claim 2, comprising a degradation time ranging from minutes to months.

5. The hydrolytically degradable hydrogel of claim 2, comprising a gelation time ranging from about 1 minute to about 22 minutes.

6. The hydrolytically degradable hydrogel of claim 2, comprising a storage modulus ranging from about 3 kPa to about 10 kPa.

7. The hydrolytically degradable hydrogel of claim 2, comprising a mesh size ranging from about 7 nm to 13 nm.

8. The hydrolytically degradable hydrogel of claim 2, further comprising a cell.

9. The hydrolytically degradable hydrogel of claim 2, further comprising a protein.

10. The hydrolytically degradable hydrogel of claim 2, further comprising a drug.

11. A method of preparing a hydrolytically degradable hydrogel, the method comprising:
providing a hydrogel precursor solution, the hydrogel precursor solution comprising a polymer;
providing to the hydrogel precursor solution a crosslinker of formula (I),

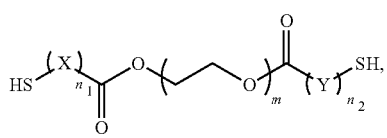

wherein m is at least 10 repeating units; $n_1$ and $n_2$ ranges from 1 to 5 repeating units; X and Y are independently selected from $CHR^1$, $NR^2$, O, $SR^3$, and aryl; $R^1$ is selected from alkyl, alkoxy, aryl, hydroxyl, amino, nitro, carboxyl, a halogen, a polar pendant group, and a non-polar pendant group; and $R^2$, and $R^3$ are independently selected from H, alkyl, alkoxy, aryl, hydroxyl, amino, nitro, carboxyl, a halogen, a polar pendant group, and a non-polar pendant group; and allowing the hydrogel precursor solution and crosslinker to polymerize to form a hydrolytically degradable hydrogel.

12. The method of claim 11, wherein the hydrogel precursor solution comprises at least one of poly(enthylene glycol)-di-acrylate (PEG-DA), multi-arm poly(ethylene glycol)-acrylate (PEG-Ac), poly(ethylene glycol)-dithiol (PEG-diSH), poly(ethylene glycol) divinyl sulfone (PEG-diVS), multi-arm poly(ethylene glycol) vinyl sulfone (PEG-VS), poly(enthylene glycol)-di-methacrylate (PEG-DMA), multi-arm poly(ethylene glycol)-methacrylate (PEG-MAc), poly(ethylene glycol)-di-allyl ether (PEG-diAE), multi-arm poly(ethylene glycol)-allyl ether (PEG-AE), poly(ethylene glycol)-di-vinyl ether (PEG-diVE), multi-arm poly(ethylene glycol)-vinyl ether (PEG-VE), poly(ethylene glycol)-di-maleimide (PEG-diMI), multi-arm poly(ethylene glycol)-maleimide (PEG-MI), poly(ethylene glycol)-di-norborene, multi-arm poly(ethylene glycol)-norborene, poly(ethylene glycol)-di-vinyl carbonate, multi-arm poly(ethylene glycol)-vinyl carbonate, and polyethylene glycol oligofumarate.

13. The method of claim 11, wherein the hydrolytically degradable hydrogel has a degradation time ranging from minutes to months.

14. The method of claim 11, wherein the hydrolytically degradable hydrogel has a gelation time ranging from about 1 minute to about 22 minutes.

15. The method of claim 11, wherein the hydrolytically degradable hydrogel has a storage modulus ranging from about 3 kPa to about 10 kPa.

16. The method of claim 11, wherein the hydrolytically degradable hydrogel has a mesh size ranging from about 7 nm to 13 nm.

17. The method of claim 11, further comprising adding a cell to at least one of the hydrogel precursor solution, the crosslinker, and the hydrolytically degradable hydrogel.

18. The method of claim 11, further comprising adding a protein to at least one of the hydrogel precursor solution, the crosslinker, and the hydrolytically degradable hydrogel.

19. The method of claim 11, further comprising adding a drug to at least one of the hydrogel precursor solution, the crosslinker, and the hydrolytically degradable hydrogel.

\* \* \* \* \*